US007975556B2

(12) United States Patent
Hatami et al.

(10) Patent No.: US 7,975,556 B2

(45) Date of Patent: Jul. 12, 2011

(54) SENSOR-ENABLED GEOSYNTHETIC MATERIAL AND METHOD OF MAKING AND USING THE SAME

(75) Inventors: Kianoosh Hatami, Norman, OK (US); Brian Grady, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 12/354,828

(22) Filed: Jan. 16, 2009

(65) Prior Publication Data

US 2010/0180691 A1 Jul. 22, 2010

(51) Int. Cl.
*G01N 3/00* (2006.01)

(52) U.S. Cl. ........................................................ 73/788

(58) Field of Classification Search .................... 73/760, 73/788, 795

See application file for complete search history.

(56) References Cited

U.S. PATENT DOCUMENTS

| | | | | |
|---|---|---|---|---|
| 4,947,470 | A * | 8/1990 | Darilek | 324/557 |
| 5,288,168 | A * | 2/1994 | Spencer | 405/54 |
| 5,362,182 | A * | 11/1994 | Hergenrother | 405/129.5 |
| 5,540,085 | A * | 7/1996 | Sakata et al. | 73/49.2 |
| 5,567,932 | A * | 10/1996 | Staller et al. | 250/227.14 |
| 5,989,700 | A * | 11/1999 | Krivopal | 428/323 |
| 6,056,477 | A * | 5/2000 | Ueda et al. | 405/54 |
| 6,276,214 | B1 * | 8/2001 | Kimura et al. | 73/795 |
| 6,643,532 | B2 * | 11/2003 | Axelgaard | 600/391 |
| 7,194,912 | B2 * | 3/2007 | Jordan et al. | 73/774 |
| 7,278,324 | B2 * | 10/2007 | Smits et al. | 73/799 |
| 7,402,264 | B2 * | 7/2008 | Ounaies et al. | 252/511 |
| 7,527,751 | B2 * | 5/2009 | Ounaies et al. | 252/511 |
| 7,532,780 | B2 * | 5/2009 | Delmas et al. | 385/13 |
| 7,663,381 | B2 * | 2/2010 | Watkins et al. | 324/693 |
| 7,673,521 | B2 * | 3/2010 | Ajayan et al. | 73/774 |
| 7,849,751 | B2 * | 12/2010 | Clark et al. | 73/768 |
| 2003/0039816 | A1 * | 2/2003 | Wang et al. | 428/299.1 |
| 2004/0239475 | A1 * | 12/2004 | Hermann et al. | 338/25 |
| 2005/0284232 | A1 * | 12/2005 | Rice | 73/762 |
| 2006/0184067 | A1 * | 8/2006 | Clark et al. | 600/587 |
| 2007/0279632 | A1 * | 12/2007 | Delmas et al. | 356/429 |
| 2008/0191177 | A1 * | 8/2008 | Mainwaring et al. | 252/511 |

* cited by examiner

*Primary Examiner* — Freddie Kirkland, III

(74) *Attorney, Agent, or Firm* — Hall Estill Law Firm

(57) ABSTRACT

The present invention is directed to a sensor-enabled geosynthetic material for use in geosynthetic structures, a method of making the sensor-enabled geosynthetic material, and a method of measuring geometric strains of a geosynthetic product made from the sensor-enabled geosynthetic material. The sensor-enabled geosynthetic material includes a polymeric material and an electrically conductive filler. The polymeric material and an electrically conductive filler are combined to provide a sensor-enabled geosynthetic material. The sensor-enabled geosynthetic material having a predetermined concentration of the electrically conductive filler so as to provide the sensor-enabled geosynthetic material with an electrical conductivity and a strain sensitivity within the percolation region or slightly above it.

18 Claims, 22 Drawing Sheets

SENSOR-ENABLED GEOSYNTHETIC MATERIAL AND METHOD OF MAKING AND USING THE SAME

STATEMENT REGARDING FEDERALLY SPONSORED RESEARCH OR DEVELOPMENT

Not Applicable.

CROSS-REFERENCE TO RELATED APPLICATIONS

Not Applicable.

BACKGROUND OF THE INVENTION

1. Field of the Invention

The present invention relates to a sensor-enabled geosynthetic material used to construct geosynthetic structures (i.e. geotechnical structures involving geosynthetics) and a method of making the sensor-enabled geosynthetic material. Additionally, the mechanical strains of the sensor-enabled geosynthetic material can be measured or monitored without the need for conventional instrumentation.

2. Description of the Related Art

Geosynthetics are polymer-based products specifically manufactured to serve a wide range of applications in civil and environmental engineering including soil stabilization and reinforcement, separation and filtration, drainage and containment. The emergence and development of geosynthetic technology has had a significant impact on the capabilities and economics of civil engineering design and construction. Increasing number of geotechnical projects involve the applications of geosynthetics as modern solutions to conventional problems with proven advantages in the construction and retrofitting of infrastructure including: ease and speed of construction, construction in difficult access locations, superior performance under static and seismic loading conditions, lower costs, reducing the size of structures and hence providing greater usable space, aesthetically pleasing appearance and blending with the environment. In several cases (e.g. geomembranes in hazardous and municipal waste containment), the use of geosynthetics is mandated by law.

Geosynthetic engineering and the related manufacturing and construction industries have experienced tremendous growth over the past few decades and are now an established technology involving billions of dollars of projects in the U.S. and worldwide. At the same time, as geosynthetic-related structures and facilities become ubiquitous, it becomes vital to ensure that these structures are not only safe but also offer a satisfactory level of serviceability through health monitoring and timely measures to prevent catastrophic failures and costly repairs due to inadequate structural performance resulting from uncertainties in site conditions, material properties and behavior, construction practice, environmental effects and loading conditions. This is especially true where these structures support crucial infrastructure in urban areas and along transportation corridors, or protect the environment from hazardous waste, leaking fuel or other contaminants. The importance of instrumentation and health monitoring of infrastructure is increasingly recognized in order to address these challenges and uncertainties to ensure the success of the project with respect to its safety and cost. An important aspect of health monitoring for geosynthetic structures is to monitor geosynthetic strain during service life and/or extreme (e.g. seismic) events.

Geosynthetics have become an indispensable part of the infrastructure development and renewal enterprise. Unfortunately, a vital aspect of sustainable development; namely, their instrumentation and health monitoring has received comparatively little attention with costly consequences. A significant predicament in performance monitoring of geosynthetic structures has been due to the fact that installation of instruments (e.g. strain gauges) are typically tedious and costly with rather unpredictable outcome. Current design guidelines for different geosynthetic structures are largely based on empirical and conventional (e.g. limit-equilibrium) approaches without proper assessment and in-depth understanding of the influence of important factors such as peak strain and in-soil properties of geosynthetics. As a result, overly conservative design procedures and reduction factors are typically imposed on the strength of the geosynthetic material to address concerns related to their durability and creep. This renders the cost of these structures in many instances much greater than necessary, and counters their intrinsic cost-effectiveness. Other important applications which could benefit significantly from a reliable health monitoring system include landfills to detect geomembrane overstress at their trenched anchors, covers or other locations (e.g. within geomembranes often buried under hundreds of feet of waste) well before the occurrence of leakage under service conditions or, e.g. following seismic events. Current technology merely involves leak detection systems which could only detect the problems in more advanced stages. Similar benefits could be achieved in geopipes, geosynthetic platforms over sinkholes and other soil stabilization, containment and storage applications.

In addition, the existing technology currently employed to measure strains in geosynthetics requires complex and expensive data acquisition systems. The existing technology for the instrumentation of geosynthetics primarily entails the attachment of strain gauges and extensometers to a geosynthetic material which are calibrated against average strains from crosshead displacement in their in-isolation tests. However, these calibration factors are not truly applicable to a geosynthetic layer embedded in soil due to at least three important reasons: 1) different in-soil mechanical properties (e.g. tensile modulus) of geosynthetics compared to their in-isolation values due to confining pressure and interlocking effects, 2) complications such as soil arching due to the mechanical interference and interaction of strain gauges and their bonding assembly (e.g. adhesive and protective sleeve) with the local soil, 3) unknown local stiffening effect of the bonding assembly. These factors can introduce significant errors in measured strains in geosynthetics in field applications. Applying in-isolation calibration factors to in-soil readout data could lead to significant underestimation of reinforcement strain and axial load with potential consequences with respect to stability and performance. Recent studies include discussions on subjects such as strain gauge calibration, local vs. global strains, under-registration of strain due to attachment technique and correction factors to estimate global strains in geosynthetic reinforcement.

In addition, geosynthetic strain is not routinely monitored in the field due to the added costs and level of care and skills required for proper installation of the instruments. Other impediments include lack of reliable strain gauging techniques and proper training of contractors, durability and reliability of instruments and requirements for time-consuming installation and protection measures. For these reasons, geosynthetic instrumentation in the field has been primarily limited to research and demonstration projects with a comparatively insignificant footprint in their mainstream construction considering the vast number of geosynthetic-related structures constructed in the U.S. In those occasions where field structures have been instrumented, the extent of instrumentation related to the geosynthetic strain data has been fairly limited. As a result, important information on the extent and distribution of strains and stresses in these structures is not typically available.

Recent attempts to measure soil strains and in-soil reinforcement strains include those involving digital imaging, X-ray and tomographical techniques in small-scale laboratory specimens. However, the limited in-soil penetration range of these techniques renders them impractical for field-scale structures. Another recent development involves the attachment of fiber optic cables to geotextiles or geomembranes. However, these techniques do not incorporate the sensing capabilities within the geosynthetic materials, and the added manufacturing and construction costs related to the fiber optic material and their installation need further analysis.

Accordingly, there remains a need for a new generation of geosynthetics having sensing capabilities embedded therein in order to measure their mechanical strain without the need for conventional instrumentation.

SUMMARY OF THE INVENTION

The present invention relates to a sensor-enabled geosynthetic material for use in geosynthetic structures. The sensor-enabled geosynthetic material is fabricated from a polymeric material and an electrically conductive filler combined with the polymeric material. The sensor-enabled geosynthetic material fabricated has a predetermined concentration of the electrically conductive filler contained therein so as to provide the sensor-enabled geosynthetic material with electrical conductivity, as well as electrical conductivity that changes with strain.

In another embodiment of the present invention, a method of making the sensor-enabled geosynthetic material is provided. The sensor-enabled geosynthetic material is fabricated by providing a polymeric material and an electrically conductive filler. Once the polymeric material and the electrically conductive filler are provided, the polymeric material and the electrically conductive filler are mixed to provide the sensor-enabled geosynthetic material. The sensor-enabled geosynthetic material having a predetermined concentration of the electrically conductive filler so as to provide the sensor-enabled geosynthetic material with electrical conductivity, as well as electrical conductivity that changes with strain.

In a further embodiment of the present invention, a method of measuring geometric strains of a geosynthetic product is provided. To measure the geometric strains of a geosynthetic product a geosynthetic product is provided from fabricating a sensor-enabled geosynthetic material. Once the geosynthetic product is provided, a measuring location of the geosynthetic product is selected to measure the geometric strain. Then, the geometric strains of the geosynthetic product are determined at the measuring location.

BRIEF DESCRIPTION OF THE DRAWINGS

FIG. 3(*b*) is a typical specimen used in the strain-resistivity tests.

FIG. 5(*b*) is a graph view showing Strain vs. Time of a loading regime for strain-sensitivity testing of a sensor-enabled geosynthetic material constructed in accordance with the present invention.

FIG. 5(*c*) is a graph view showing Force vs. Strain of a loading regime for strain-sensitivity testing of a sensor-enabled geosynthetic material constructed in accordance with the present invention.

FIG. 6(*b*) is a graph view showing the surface conductivity of a sensor-enabled geosynthetic material constructed in accordance with the present invention.

FIG. 7(*b*) is a graph view showing the tensile strength of another embodiment of the sensor-enabled geosynthetic material constructed in accordance with the present invention.

FIG. 7(*c*) is a graph view showing the failure strain of a sensor-enabled geosynthetic material constructed in accordance with the present invention.

FIG. 7(*d*) is a graph view showing the failure strain of another embodiment of the sensor-enabled geosynthetic material constructed in accordance with the present invention.

FIG. 8(*b*) is a graph view showing strain-resistivity of another embodiment of the sensor-enabled geosynthetic material constructed in accordance with the present invention.

FIG. 8(*c*) is a graph view showing strain-resistivity of yet another embodiment of the sensor-enabled geosynthetic material constructed in accordance with the present invention.

FIG. 8(*d*) is a graph view showing strain-resistivity of a further embodiment of the sensor-enabled geosynthetic material constructed in accordance with the present invention.

FIG. 9(*b*) is a graph view showing tensile responses of another embodiment of the sensor-enabled geosynthetic material constructed in accordance with the present invention.

DETAILED DESCRIPTION OF THE INVENTION

Figure 1:
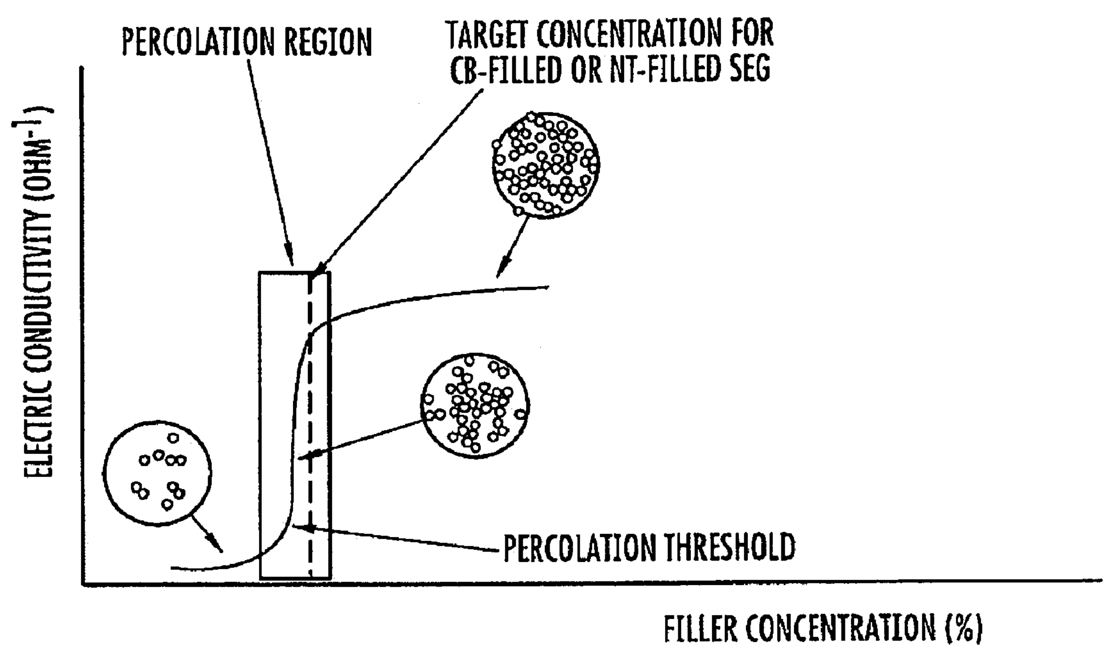
FIG. 1 is a graph view showing the percolation threshold and the percolation region of a sensor-enabled geosynthetic material.

The present invention relates to a sensor-enabled geosynthetic (SEG) material used for constructing geosynthetic structures, such as geogrids and geomembranes, which are used in reinforcement and containment applications. The sensor-enabled geosynthetic material is embedded with sensing capabilities in order to measure the mechanical strains subjected on the geosynthetic structures at any location of the geosynthetic structures. As the mechanical strains on a geosynthetic structure change, the conductivity of the sensor-enabled geosynthetic material is affected.

Generally, the sensor-enabled geosynthetic material includes a polymeric material (or geosynthetic material) and an electrically conductive filler. The polymeric materials used in geosynthetic structures are typically electrically insulating materials. An electrically conductive filler is added to the polymeric material in sufficient amounts to transform the polymeric material from an insulating material into a conductive material. The addition of the electrically conductive filler to the polymeric material would transform the polymeric material into the sensor-enabled geosynthetic material, which allows the geosynthetic material to be self instrumented or "sensor-enabled" and amenable to strain-monitoring at virtually any location within the geosynthetic material. The addition of the electrically conductive filler to the polymeric material increases the conductivity of the polymeric material substantially (e.g. by several orders of magnitude).

The polymeric material can be any polymer or combination of polymers that provide the necessary structure requirements needed for a given use of a geosynthetic structure. Examples of polymers that can be used as polymeric material include, but are not limited to, polyolefin polymers. Examples of polyolefin polymers include polyethylene (PE), high-density polyethylene (HDPE), polypropylene (PP) and the like. In some instances, the polymeric material is provided from commercial manufacturers having electrically conductive filler contained therein.

The electrically conductive filler can be any material capable of being mixed with the polymeric material to provide a sensor-enabled geosynthetic material which is conductive. Examples of electrically conductive fillers include, but are not limited to, metal powders, conductive carbon black (CB), graphite fiber, carbon nanotubes (NT), and the like. Further, specific examples of carbon nanotubes include, but are not limited to, single-walled nanotubes and multi-walled nanotubes. The electrically conductive filler can be provided in any form that can create a network of conductive linkages throughout the polymeric material. For example, the electrically conductive filler can be provided in the form of particles, particulates, aggregates, fibers, and the like.

As the concentration of the electrically conductive filler dispersed in the polymeric material is increased from zero (i.e. amount of electrically conductive filler in a virgin polymeric material), insulating gaps along pathways of the electrically conductive filler in the polymeric material eventually disappear or become less than some critical value (e.g. 10 nm). At a critical concentration of the electrically conductive filler in the polymeric material, the electrically conductive fillers form a network of conductive linkages which allows the electrons to be able to pass through the sensor-enabled geosynthetic material.

Referring now to the drawings, and more particularly to FIG. 1, shown therein is a graph depicting the relationship between the concentration of the electrically conductive filler in the polymeric material and the electric conductivity of the resulting sensor-enabled geosynthetic material. The smallest concentration of the electrically conductive filler in the polymeric material which allows the continuous network of conductive pathways to be established within the sensor-enabled geosynthetic material is called the percolation threshold. Once the concentration of the electrically conductive filler in the sensor-enabled geosynthetic material passes the percolation threshold, the sensor-enabled geosynthetic material enters into a percolation region. The conductivity of the sensor-enabled geosynthetic material in the percolation region (a range of electrically conductive filler concentrations) is highly sensitive to factors such as changes in the electrically conductive filler placement or mechanical strain. In the percolation region, small changes in the network structure of the electrically conductive filler (e.g. due to tensile or mechanical strain) can dramatically change the conductive pathways in the sensor-enabled geosynthetic material which, in turn, can cause large changes in conductivity. As the concentration of the electrically conductive filler in the sensor-enabled geosynthetic material reaches concentrations above the percolation region, the increased concentration of the filler in the sensor-enabled geosynthetic material will ultimately result in relatively mild improvements in conductivity but drastic reduction of strain sensitivity due to formation of denser three-dimensional networks among the electrically conductive filler.

The range of filler concentrations that defines the percolation region varies with the specific type of the electrically conductive filler that is used to construct the sensor-enabled geosynthetic material, and to a lesser extent, with the type of polymeric material. The target concentration of the electrically conductive filler in the sensor-enabled geosynthetic material is the maximum concentration of the electrically conductive filler that still places the sensor-enabled geosynthetic material within the percolation region. When the sensor-enabled geosynthetic material is provided in the upper concentration portion of the percolation region, both the electrical conductivity and the strain sensitivity of the sensor-enabled geosynthetic material are maximized.

The electrically conductive filler is provided in the sensor-enabled geosynthetic material in an amount sufficient to accomplish the functionality of the sensor-enabled geosynthetic material described herein. In one embodiment of the present invention, the electrically conductive filler is provided in the sensor-enabled geosynthetic material in a concentration of from about 0.01 wt % to about 30 wt %. In another embodiment of the present invention, the electrically conductive filler is provided in the sensor-enabled geosynthetic material at a concentration that places the piezoresistivity of the sensor-enabled geosynthetic material in the percolation region. In a further embodiment of the present invention, the electrically conductive filler is provided in the sensor-enabled geosynthetic material at a concentration that places the piezoresistivity of the sensor-enabled geosynthetic material in the upper concentration portion of the percolation region, or up to 5 wt % above the percolation region.

Another embodiment of the present invention is directed to a method of fabricating the sensor-enabled geosynthetic material. Further, a method of fabricating a geosynthetic product from the sensor-enabled geosynthetic material is provided herein. The method of fabricating the sensor-enabled geosynthetic material starts with providing the polymeric material and the electrically conductive filler. The polymeric material and the electrically conductive filler are provided in any amounts such that the concentration of the electrically conductive filler in the sensor-enabled geosynthetic material places the piezoresistivity of the sensor-enabled geosynthetic material in the percolation region or slightly above it. Once the polymeric material and the electrically conductive filler are provided, these materials are mixed to fabricate the sensor-enabled geosynthetic material. The dispersion (or mixing) of the electrically conductive filler within the polymeric material can be done in any manner that is suitable and known in the art. For example, the mixing can be carried out utilizing any melt-blending process (e.g. extrusive mixing) or compression molding. Once the sensor-enabled geosynthetic material has been fabricated from the polymeric material and the electrically conductive filler, the sensor-enabled geosynthetic material is manipulated to form a geosynthetic product, such as a geogrid or a geomembrane.

In another embodiment of the present invention, a method of measuring and/or monitoring geometric (or mechanical) strains in a geosynthetic product is provided. In the method of measuring and/or monitoring geometric (or mechanical) strains in a geosynthetic product, a geosynthetic product is constructed using a sensor-enabled geosynthetic material described herein. During the construction of a geosynthetic structure, e.g. a mechanically stabilized earth (MSE) wall, selected locations (measuring sites) within the reinforced zone constructed with the sensor-enabled geosynthetic reinforcement can be wired to monitor and measure mechanical strain. The locations for measuring strain can be any part of the layers of the geosynthetic product (or geosynthetic layers). In addition, the method of measuring and/or monitoring the geometric strain of the geosynthetic product can be done during different stages of the geosynthetic structure's construction. Furthermore, this method provides a geosynthetic product that can have its mechanical strain simultaneously measured and/or monitored at a plurality of measuring locations on the geosynthetic product.

It should be understood that the geometric strain can be determined using any known method in the art. In one embodiment of the present invention, conductive leads are attached to the geosynthetic layers at the measuring locations to provide conductivity data. The leads can be attached to the geosynthetic layers at various predetermined gauge distances to provide the conductivity data. Once the conductivity data is provided, the conductivity data is manipulated to provide the geometric strain of the geosynthetic structure at the measuring location. This method of measuring and/or monitoring the response of geosynthetic structures enhances the ability to expand an inventory of structural health monitoring data to gain advantages which include: (1) developing a more accurate understanding of geosynthetic structure's mechanical behavior during construction, at service load levels and under extreme events such as earthquake and blast loading, (2) creating a database of performance results that could be used to validate analytical and computational models, and (3) improving current design methodologies for geosynthetic structure's construction and retrofitting by developing performance-based design approaches that would be more rational and economical.

In a further embodiment of the present invention, the conductivity data and the geometric strain data obtained from the measuring sites of the geosynthetic structure can be compiled and stored. The conductivity data and the geometric strain data can be compiled and stored for any purpose known in the art, such as those described above.

Figure 2:
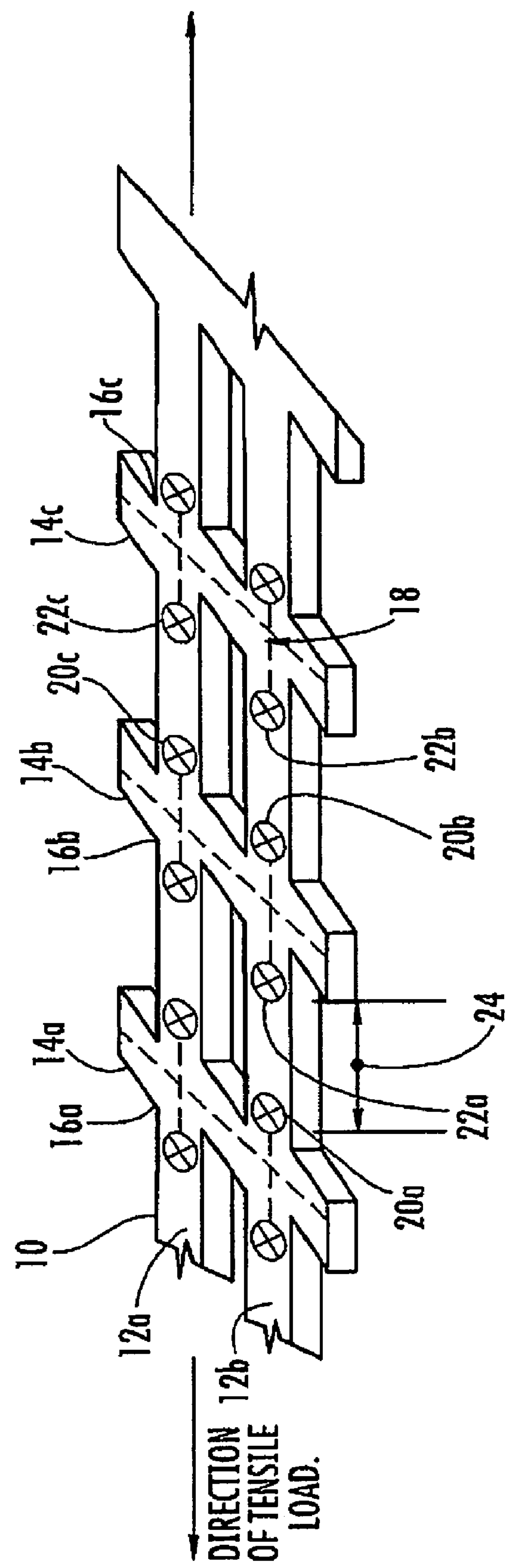
FIG. 2 is a pictorial representation of a geosynthetic structure constructed in accordance with the present invention.

Referring now to FIG. 2, shown therein is an example of a geogrid 10 (geosynthetic product) setup to measure its geometric strains. The geogrid 10 is comprised of a plurality of longitudinal ribs 12 and a plurality of cross ribs 14, only three of the longitudinal ribs 12 and the cross ribs 14 being labeled in FIG. 2 by reference numerals 12*a* and 12*b* and 14*a*, 14*b*, and 14*c*, respectively, for purposes of clarity. Geogrid junctions 16 are created where the longitudinal ribs 12 and the cross ribs 14 intersect, only three of the geogrid sections 16 being labeled in FIG. 2 by reference numerals 16*a*, 16*b*, and 16*c* for purposes of clarity. To measure the geogrid's 10 geometric strain, the geogrid 10 is provided with wiring 18 and a plurality of pairs of electric terminals 20 and 22 for attaching the conductive leads, only three of the pairs of electronic terminals 20 and 22 being labeled in FIG. 2 by reference numerals 20*a* and 22*a*, 20*b* and 22*b*, and 20*c* and 22*c* for purposes of clarity. The electronic terminals 20 and 22 are separated by a gauge length 24. Across the gauge length 24 is where the geometric strain of the geogrid 10 (or geosynthetic product) is measured and/or monitored. It should be understood and appreciated that while FIG. 2 shows a specific example of how to setup a geosynthetic product to be measured and/or monitored, the geosynthetic product can be setup to be measured and/or monitored by any manner known in the art to measure the geometric strain across a given gauge length of the geosynthetic structure.

Procedure Used to Develop Sensor-Enabled Geosynthetics

Overview

The following four series of tests were carried out as described in the following sections to develop the Sensor-Enabled Geosynthetic (SEG) materials (or specimens) and determine their conductive and tensile strength properties: 1) Test I: conductivity tests to determine the percolation threshold of each polymer-filler composite and to develop the corresponding SEG prototype (i.e. the composite with optimal filler concentration), 2) Test II: tensile tests according to the ASTM D1708 test protocol to examine the polymer-filler compatibility, 3) Test III: strain-conductivity tests on the SEG specimens to establish the proof-of-concept of measuring geosynthetic strains subjected to tensile loads without the use of conventional instruments (e.g. strain gauges and extensometers) and, 4) Test IV: tensile tests on selected SEG geogrids according to the ASTM D6637 test protocol to examine their mechanical response.

Materials

Two main categories of SEG materials discussed in this disclosure are the polymers with nanotube (NT) fillers and those with carbon black (CB) fillers. The original polymers used to develop SEG specimens included ethylene-vinyl acetate (EVA) filled with 25% by weight multi-walled carbon nanotubes (NT), polypropylene (PP) filled with 20% by weight NT, high-density polyethylene (HDPE) filled with carbon black (CB) and polypropylene filled with CB. These materials were supplied by commercial manufacturers and are recommended for compounding (i.e. diluting) with the corresponding virgin polymers (i.e. polymers with no conductive fillers). The virgin polymers used were PP and HDPE, which were also supplied by commercial manufacturers.

Unlike the samples with NT fillers, weight compositions (i.e. filler concentrations or loadings) for the CB-filled samples were not disclosed to the authors by the supplying companies. In addition, details regarding the dispersion technique of the fillers within the masterbatches are proprietary. Therefore, the CB-filled samples in this paper are identified by their "masterbatch"-to-"virgin polymer" mixing ratios instead of actual concentrations. The term masterbatch, as used herein, refers to a polymer with either a known or undisclosed filler concentration in as-supplied condition.

Test Series I: The Search for the Percolation Threshold

Mixing of Polymers and Conductive Fillers

In order to find the percolation threshold and the target filler concentration for each type of polymer, several samples were produced at different filler concentrations (NT) or mixing ratios (CB) as presented later in FIGS. 6 and 7. These mixing ratios and concentration values were chosen to give an adequate number of data points within and near the percolation region so that the shape of this region could be determined with reasonable accuracy.

Each masterbatch was first manually mixed with the corresponding virgin polymer in a container until the polymer beads appeared to be evenly distributed in the mix. The mix was subsequently extruded using a Killion KL-100 single-screw extruder (Killion/Davis-Standard 2008) with a mixing section. In addition, as is commonly practiced when a single-screw extruder is used for compounding, each composite batch produced in this study was extruded twice to enhance the uniformity of the mix. Extrusive mixing is known to be the most common method to disperse carbon black (CB) within polymers and it has been shown that multiple extrusion of filled samples can help reduce the standard deviation of conductivity measurements. However, over mixing is not desirable and can result in reduced electrical conductivity and strain sensitivity in the filled composites by increasing the gap between the conductive particles. The temperatures in the four zones of the extruder were selected based on the recommended values for injection molding of these polymers and after preliminary investigation of the quality of the extruded mix so that all polymer pellets in the batch would be preheated and melted completely and uniformly. A heated die at the final stage helped with the flow of the batch out of the extruder without the risk of burning the material. Once extruded, the samples were cooled in a cold water bath and were subsequently pelletized using a Wayne pelletizer.

Fabrication of Specimens and Conductivity Tests

Fifty-millimeter diameter, disk-shape polymeric specimens were compression molded by subjecting them to a 44.5 kN compressive force (equivalent to 22 MPa compressive stress) at 180° C. for 10 minutes using a Carver Model M laboratory press and heated plates. The compression molding technique has been used successfully in the past to produce polymer/filler blends and has been reported to result in relatively low percolation concentrations. For instance, polyethylene (PE)/CB composites have been produced using compression molding. Compression molding has been used to blend nylon powder and CB and has resulted in significantly lower percolation concentration (i.e. 9% by weight) that would have been expected using a melt-blending approach (i.e. 25% by weight).

Conductivity tests were carried out by taking resistivity measurements using a Keithley 610C Electrometer equipped with a Model 6105 Resistivity Adapter. Conductivity of each specimen was readily calculated by inverting the value of its resistivity measured from the test. Both types of surface and volume conductivity tests were carried out on the specimens by setting up a voltage difference across the specimen and measuring the electric current passing through it using the electrometer.

In addition, the specimens' conductance values were measured using an alternative method in which the voltage source was disconnected and the electrometer was used to measure the electrical resistance between the same two locations on the specimen. The first method is the recommended method for measuring the conductivity of the specimens because it directly provides the specimen conductivity which is independent of the specimen size. However, electrical resistance data from the second method (which unlike conductivity is a size-dependent parameter) showed good corroboration with the first method in detecting the percolation threshold of the tested specimens and provided additional confidence in the test results. Three independent volume and surface resistance measurements were taken on each side of every specimen in order to increase the accuracy of the measured conductivity values. In addition, conductivity tests were carried out on two nominally identical specimens for each of the five filler concentration levels (i.e. 10 specimens in total) to increase confidence in the measured data.

Test Series II: Fabrication and Tensile Testing of Polymer Specimens According to ASTM D1708

Figure 3:
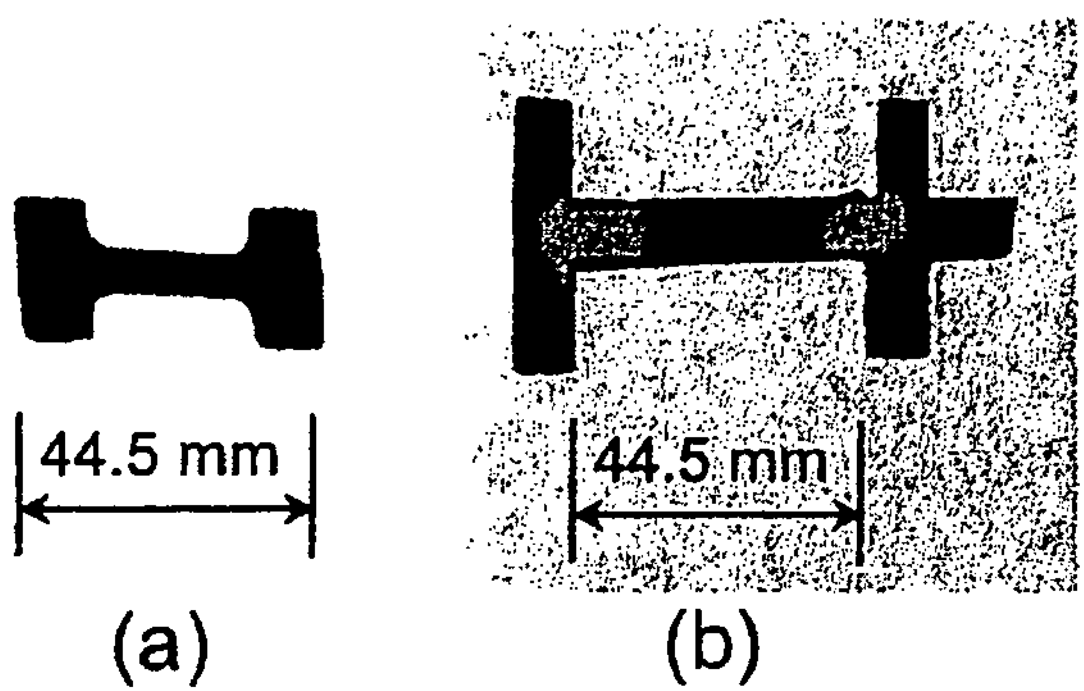
FIG. 3(*a*) is a is a test specimen in accordance with ASTM D1708.
Figure 4A:
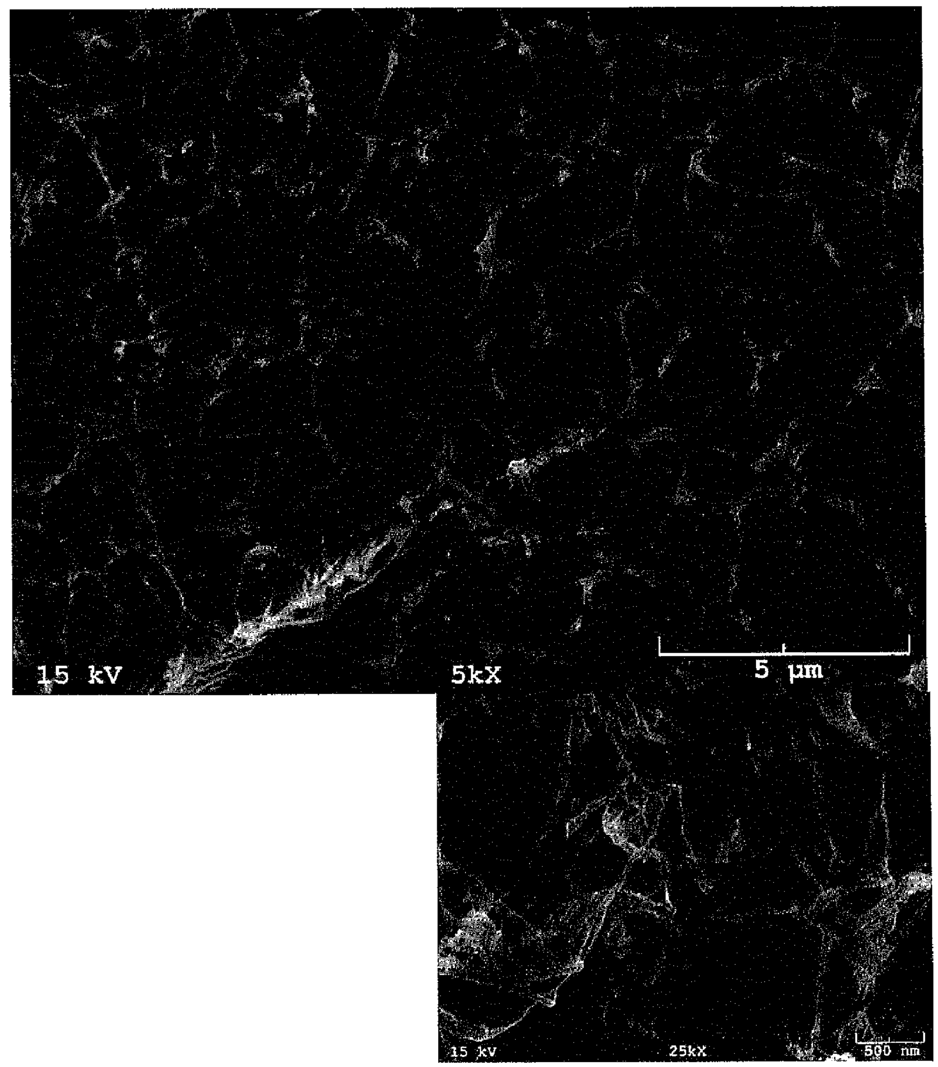
FIGS. 4(*a*)-4(*d*) show a panel of scanning electron micrographs (SEM) showing sensor-enabled geosynthetic material specimens constructed in accordance with the present invention.
Figure 4B:
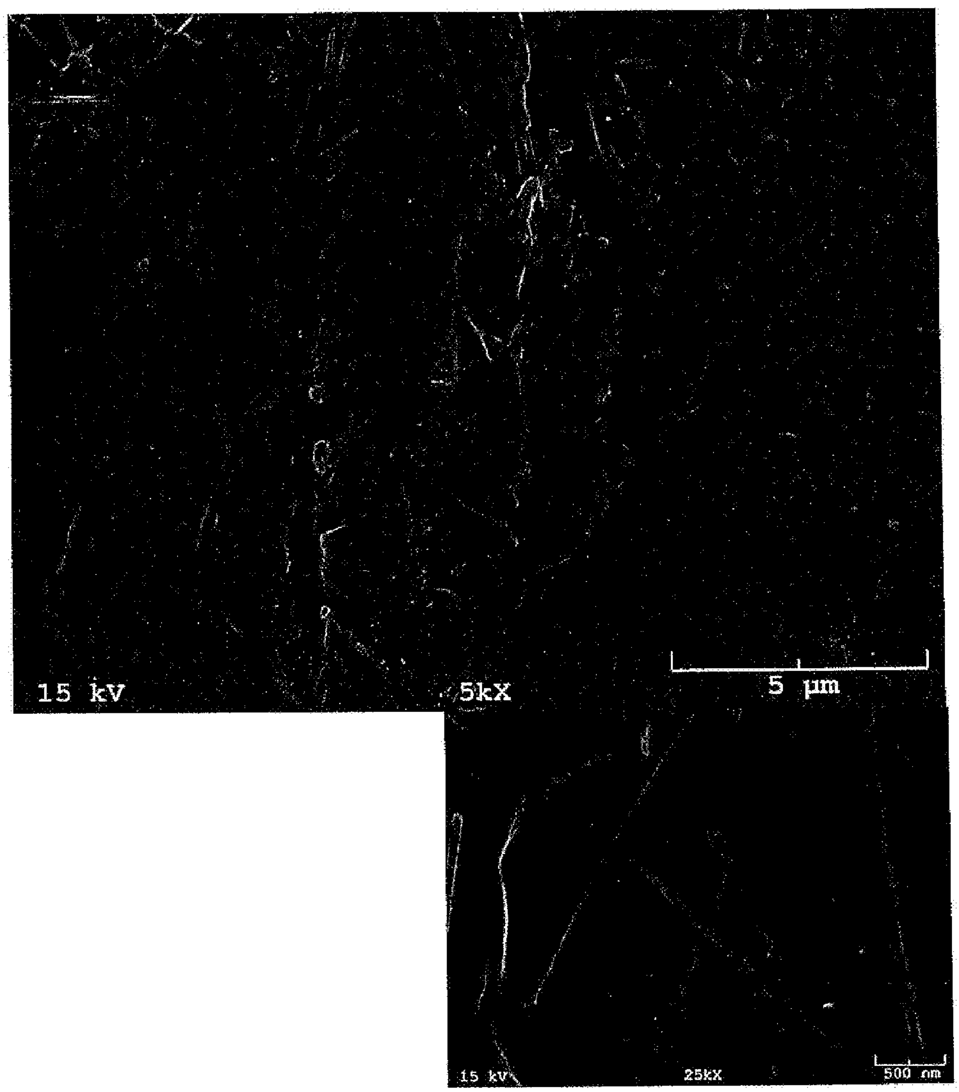
Figure 4C:
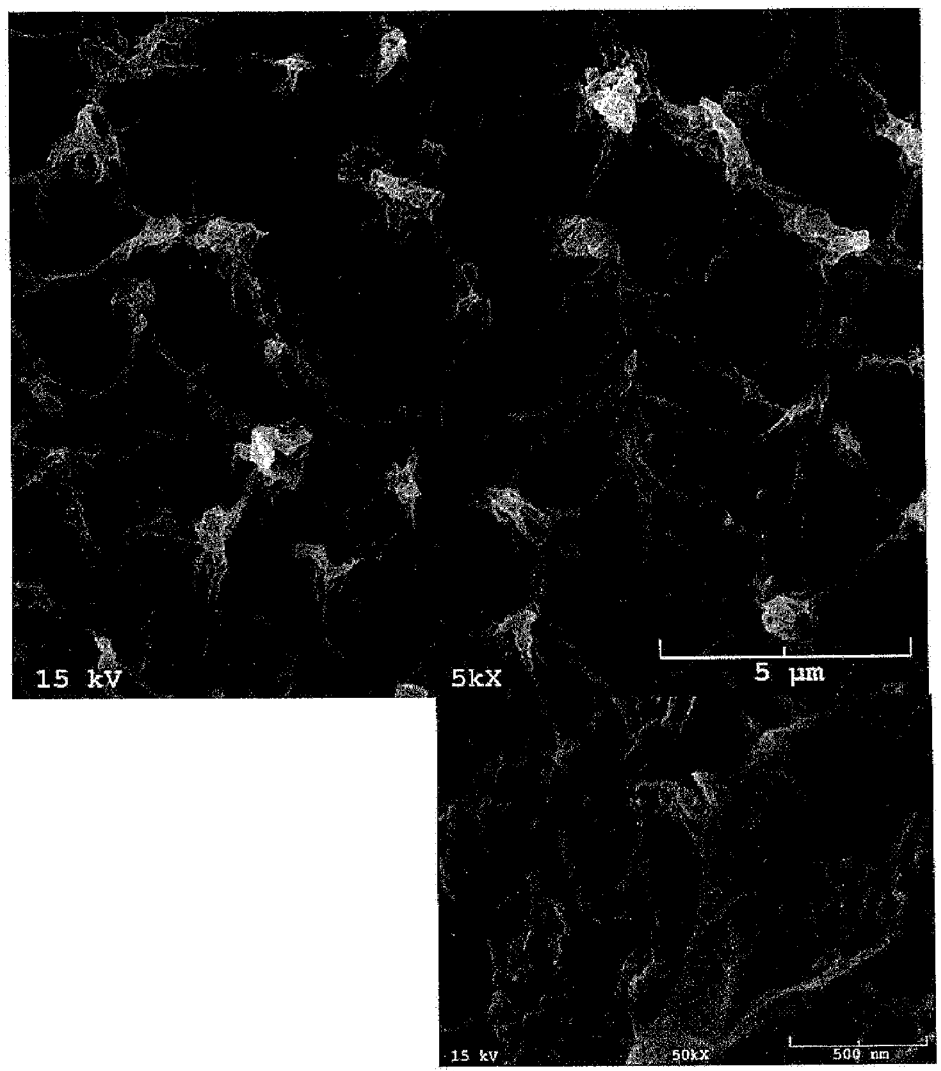
Figure 4D:
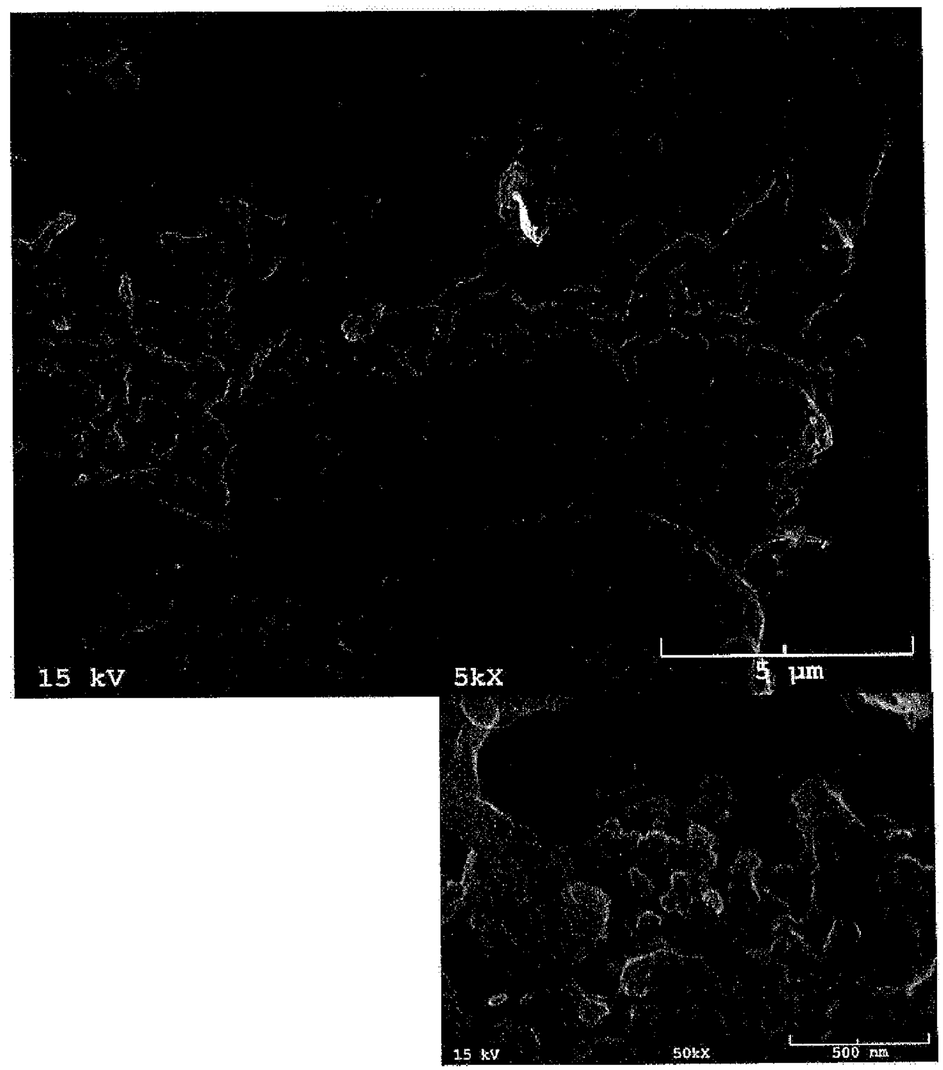

The same compression molding procedure was used to manufacture samples for both conductivity and tensile testing procedures. A 1.5-ton manual expulsion die cutter was used to cut the individual ASTM D1708 specimens (FIG. 3*a*) from the disc using a specially manufactured die. Serrated metal grips were attached to the specimens with a slight amount of tab showing in accordance with the ASTM D1708 test protocol. The position of the grips were adjusted at very small increments until the force on the sample was approximately zero, and then samples were strained at a rate of 10% per minute until failure.

Test Series III: Fabrication and Proof-of-Concept Testing of SEG Specimens

Prototype geogrids (both HDPE and PP) with filler concentrations determined from the percolation diagrams (shown later in FIG. 6) were manufactured using the mold described herein. Strain-controlled tensile tests, as described later in this section, were carried out on the 4.38% NT/HDPE, 2.8% NT/PP, 50/50 CB/HDPE and 33/67 CB/PP (i.e. SEG) specimens while their resistivity was measured simultaneously. Data from these tests were used to develop a relationship between electrical conductivity and strain for the SEG, specimens.

Molding Methodology to Manufacture SEG Specimens

Strain-conductivity measurements were carried out on single-rib SEG specimens. These specimens were made by compression molding of each polymer in an oven at 210° C. for about 35 minutes. The mold consisted of a pair of 10 cm by 10 cm aluminum plates and dead weights were used to apply normal load on the mold. One of the plates had a 3×2-aperture latticework grooving on the inside to mold the melted polymer in the shape of a geogrid with a 25.4 mm by 44.5 mm aperture size. The width of the grooving was uniform and equal to 6.4 mm throughout the molding plate. Once the specimens were completely melted and molded, the mold was removed from the oven and cooled in a water bath. The plates were then separated from each other and the geogrid specimen was carefully removed.

Scanning Electron Microscopy (SEM) Imagery

Samples of each SEG geogrid category (i.e. NT/HDPE, NT/PP, CB/HDPE and CB/PP) were frozen in liquid nitrogen and were broken to obtain (brittle) fractured cross sections. Specimens of fractured geogrid sections limited in size to 10 mm long by 3 mm wide by 1.5 mm thick were cut, dried and gold coated (to make the fractured surface conductive) for SEM imagery. Once the specimens were ready, they were mounted on bent copper strips (so-called boats) and placed inside the objective lens of a JEOL JSM-880 High Resolution Scanning Electron Microscope (SEM) with a maximum resolution of ×300,000 (SRNEML 2008). Example SEM images of the SEG specimens are presented in FIG. 4 at ×5000 magnification factor with inset images magnified by a factor of ×25,000 or ×50,000. It can be observed that both CB and NT fillers can be easily identified in the SEM images and they are both well dispersed and incorporated within the HDPE and PP polymer matrices.

Strain-Resistance Tensile Testing of SEG Specimens

Figure 5A:
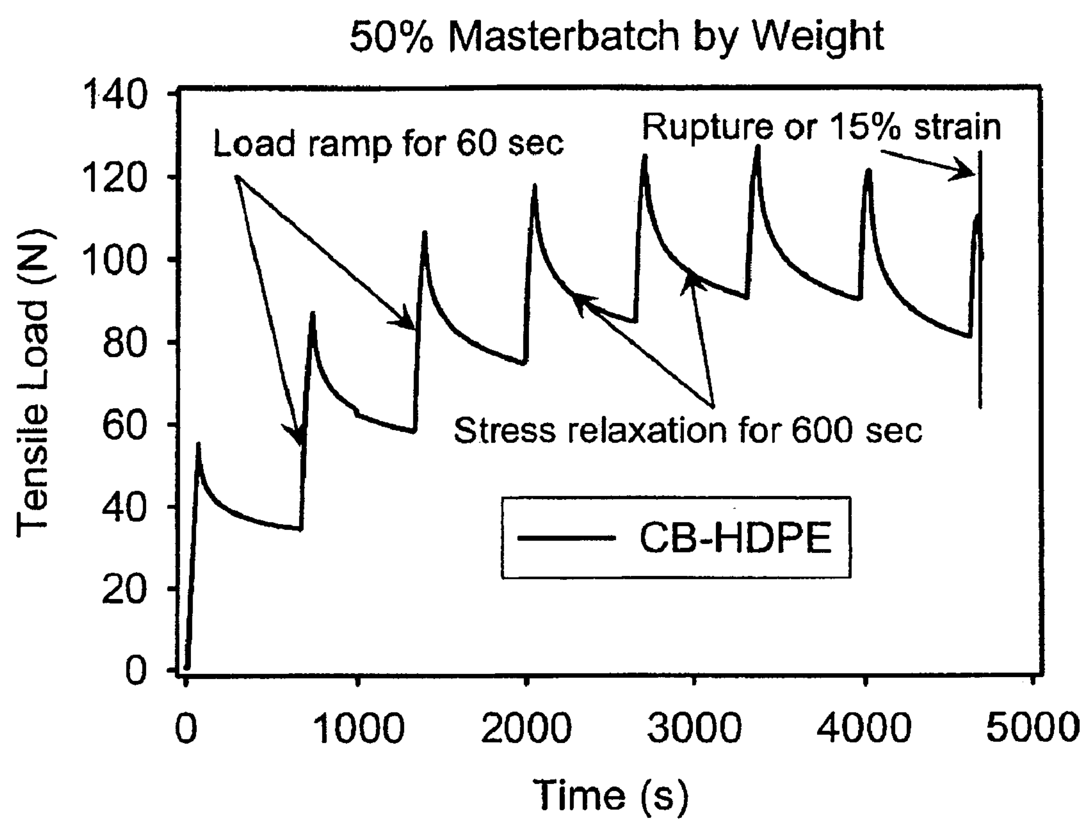
FIG. 5(*a*) is a graph view showing Force vs. Time of a loading regime for strain-sensitivity testing of a sensor-enabled geosynthetic material constructed in accordance with the present invention.
Figure 5B:
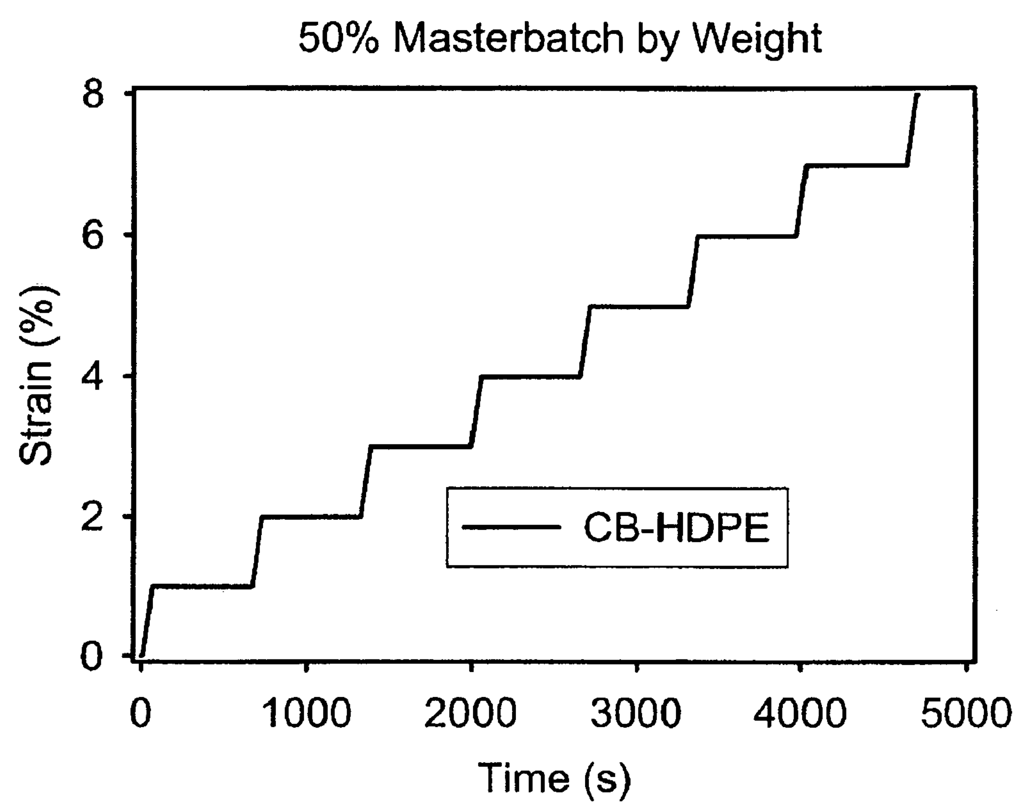
Figure 5C:
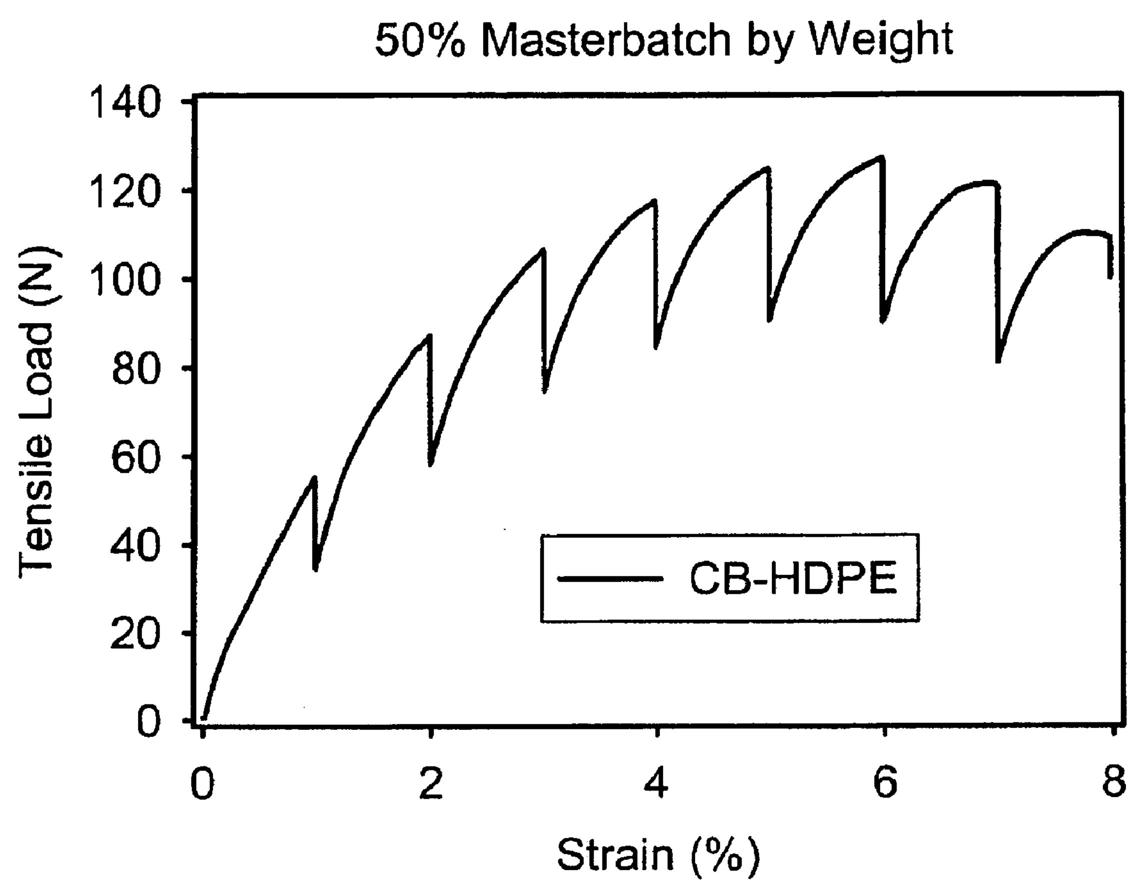

Single-rib specimens, 44.5 mm long, 6.4 mm wide and 1.35 mm thick, were cut out from the geogrids produced in the mold (FIG. 3*b*) and were set up in the tensile testing machine. Conductive leads were attached to the two ends of the specimen rib, and silver epoxy was applied to obtain reliable and highly conductive (e.g. resistivity values in the order of $10^{-4}$ Ωcm) electric connections between the leads and the polymer. Tensile testing of the specimens was carried out according to the following loading regime: The specimens were stretched at 1% strain per minute for one minute and then held at constant strain for 10 minutes (FIG. 5*a*). This loading regime was adopted in order to apply a relatively slow loading rate on the SEG specimens (simulating field conditions) and at the same time, minimize the testing time. The duration of the stress relaxation period (i.e. t=10 min) was decided after inspecting results from the preliminary tests which indicated that there would be a diminished return on the magnitude of stress relaxation beyond about 10 minutes. Any further delay in the application of the next load increment would only result in greater testing time during which the electrical conductivity of the specimen would remain almost constant. The loading pattern shown in FIG. 5*a* was repeated until the specimen strain reached 15%, or the specimen failed. Resistance measurements were taken using the electrometer at the beginning of the test and at the end of each 10-minute relaxation period. FIGS. 5*b* and 5*c* show example strain-time and load-strain responses obtained for a CB/HDPE specimen.

The electrical resistance of some SEG specimens was high enough so that the conductivity of the testing apparatus was no longer negligible. Consequently, steps were taken to electrically isolate the specimen from the testing apparatus. This was accomplished by wrapping the SEG specimens in isolating tape before installing the specimens at the clamps. Some trial attempts were needed to optimize the thickness of the isolating tapes in order to minimize the slippage of the specimens within the clamps. Similar attempts for electrical insulation of specimens have been reported in the literature.

Several specimens were observed to break gradually during testing rather than fail abruptly. When the micro-ruptures in the specimen occurred in between the electric probes, the measured resistance would show a spike in response. On the other hand, when the failing of the specimen initiated outside the span between the probes, the stress-strain curve showed a marked change while the electrical resistivity remained practically unchanged. Both of these occurrences might have contributed to the scatter in the data shown herein.

Test Series IV: Fabrication and Tensile Testing of SEG Geogrids According to ASTM D6637

A series of tensile tests were carried out to investigate the mechanical response of the SEG geogrids according to the ASTM D6637 test protocol. The geogrid specimens needed for these tests were manufactured by pressing pellets using a Model TEG Baldwin-Tate universal testing machine. The specimens were placed in a specially grooved aluminum-plate mold and pressed at 180° C. with 4.45 kN force for 15 minutes. The mold contained a 7×5-apperture grooved latticework that was 350 mm long and 250 mm wide with the grooving width of 3 mm and aperture size of 41 mm by 25 mm. Heating was provided by a Barnstead Thermolyne SRL12241 heating mat with pieces of plywood placed on the top and bottom of the setup to serve as insulation layers. A J-KEM Scientific Model 210 temperature controller was used to control the specimen temperature. After the mold was removed from the setup, it was immediately submerged in a water bath for cooling. Single-rib SEG specimens were cut out of the fabricated grids according to Method A as described in the D6637 test protocol and strained at a rate of 10% per minute until failure.

Results and Discussion

Test Series I: Percolation Threshold Results

Figure 6A:
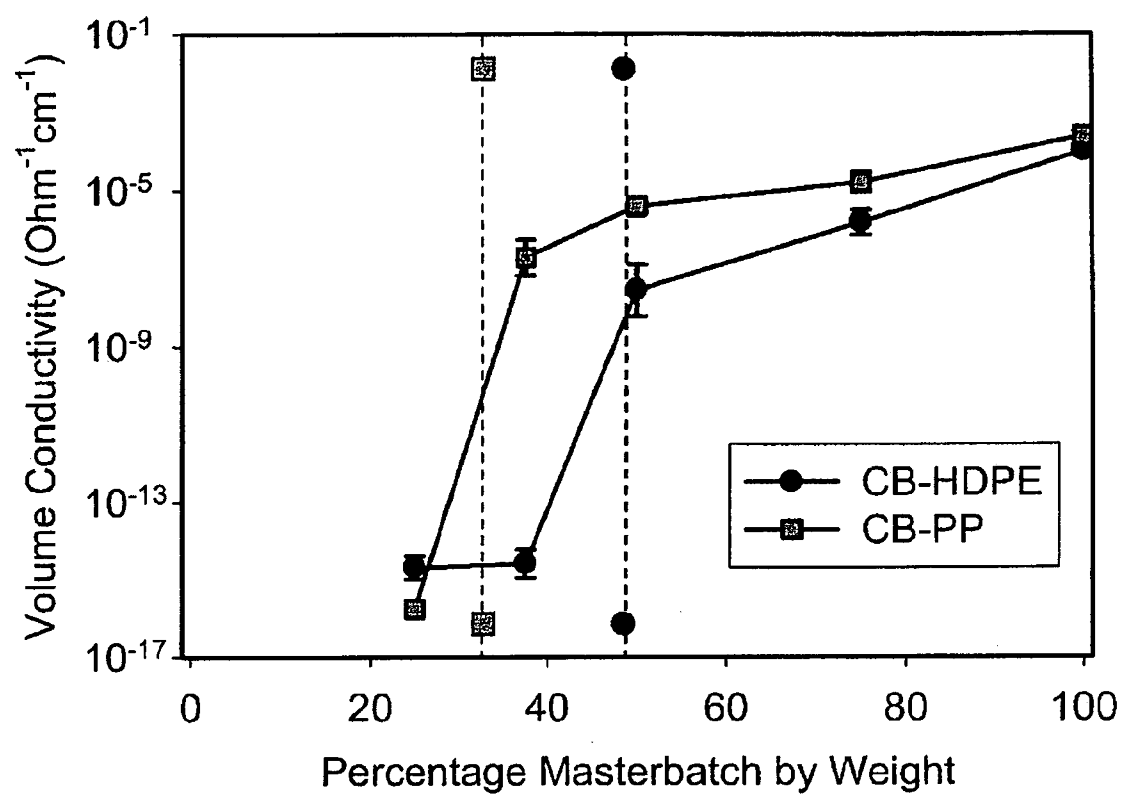
FIG. 6(*a*) is a graph view showing the volume conductivity of a sensor-enabled geosynthetic material constructed in accordance with the present invention.
Figure 6B:
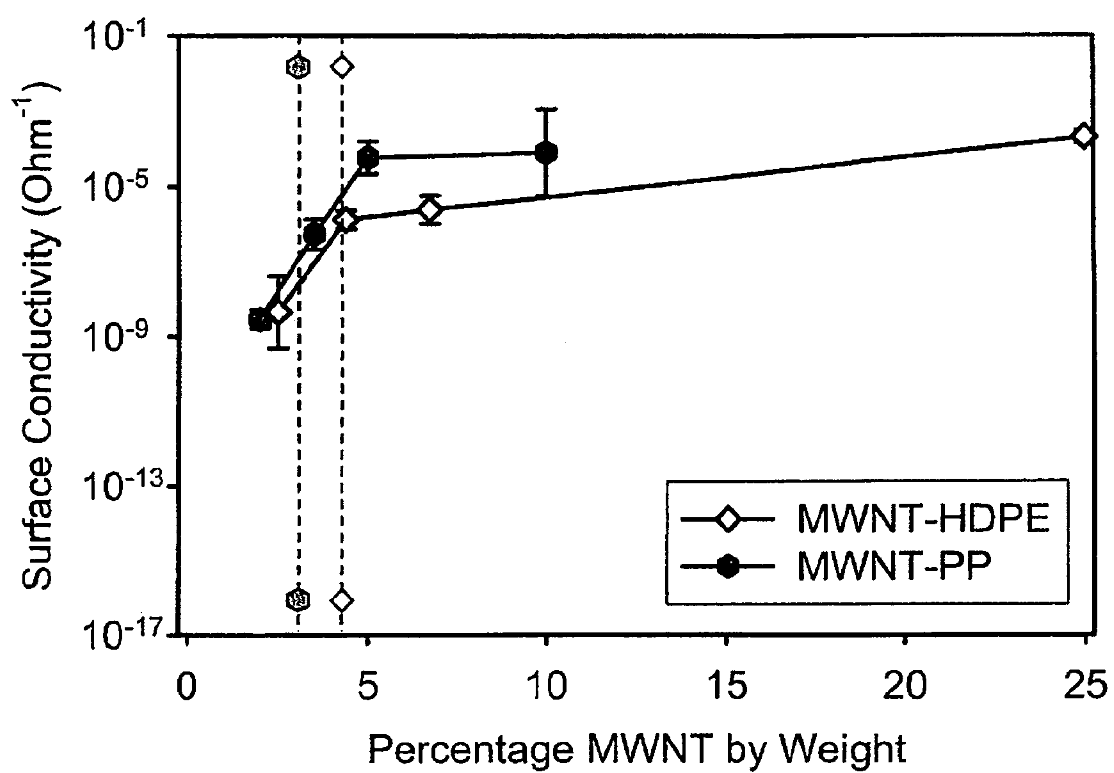

FIG. 6 shows example volume and surface conductivity results for the CB-filled and NT-filled polymers tested in this study. Results shown in FIG. 6 represent typical conductivity-concentration plots in which the percolation regions are clearly identifiable. The results obtained from the surface and volume conductivity tests were consistent with each other for each of the CB-filled and NT-filled polymers tested. Optimum concentration values (i.e. to simultaneously maximize the strain sensitivity and magnitude of the specimen conductivity) for the NT/PP and NT/HDPE materials were found to be 2.8% and 4.38%, respectively. The optimum mixing ratio values for the CB/PE and CB/PP specimens were found to be 50/50 and 33/67, respectively. These optimum values (used to fabricate the SEG specimens) are indicated with dashed lines on the plots in FIG. 6. It should be noted that the accuracy of optimum concentration and mixing ratio values reported above corresponds to the number of data points reported in FIG. 6 and these optimum values could be fine tuned by mixing the corresponding conductive fillers at slightly different concentrations. However, the differences in conductivity due to sample preparation procedures are believed to overshadow any errors in the optimum values reported above.

Test Series II: Tensile Response of CB-Filled and NT-Filled Polymers (ASTM D1708)

FIG. 7 shows the tensile test results obtained for the CB-filled and NT-filled polymer specimens. Results shown in FIG. 7*a* indicate that the CB/PP specimens manufactured in this study failed at significantly lower tensile loads (e.g. about 1/3) compared to the as-supplied specimens (i.e. compared to both virgin and masterbatch specimens). This observation suggests that the two PP polymers (i.e. virgin and masterbatch) are not very compatible. On the other hand, tensile strength values obtained for the corresponding CB/HDPE specimens at different concentration levels were within the range of values obtained for the virgin and masterbatch specimens. Results shown in FIGS. 7*a* and 7*b* indicate that filler concentration influenced the tensile strength of the PP specimens more significantly than the HDPE specimens. For instance, tensile strength values of NT-filled PP specimens at the percolation threshold are approximately half as large as those for virgin PP specimens.

Figure 7A:
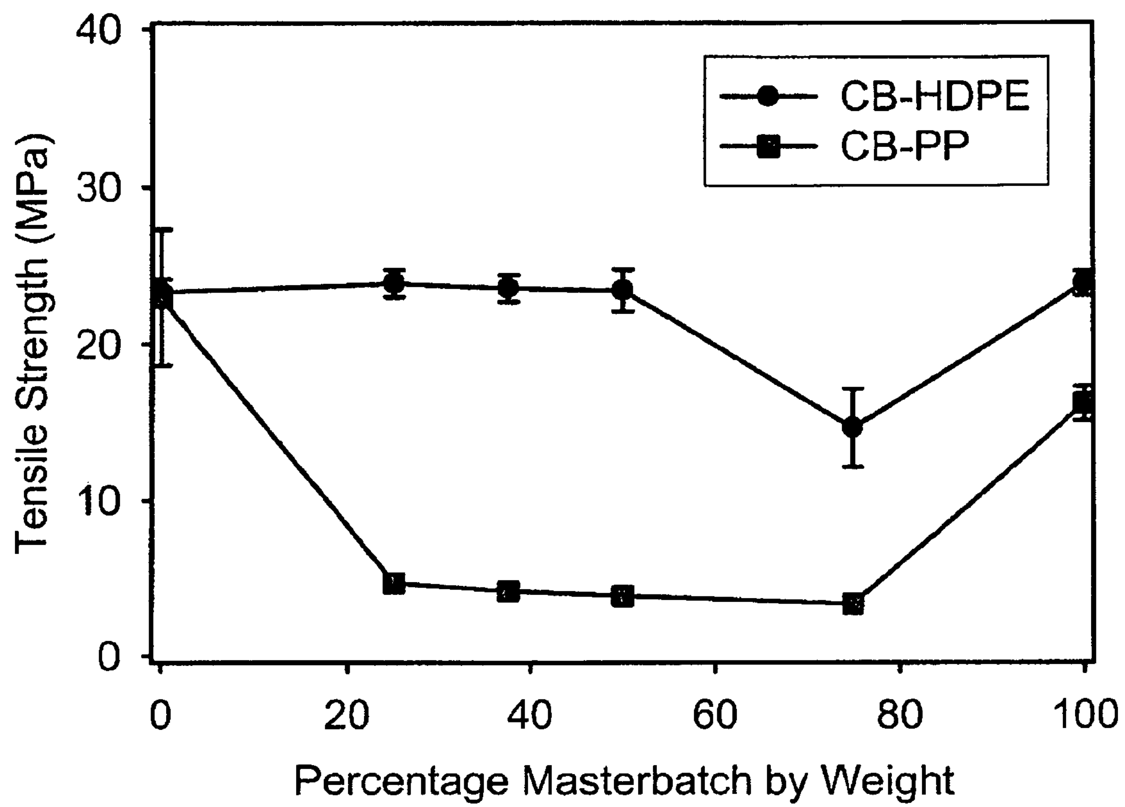
FIG. 7(*a*) is a graph view showing the tensile strength of a sensor-enabled geosynthetic material constructed in accordance with the present invention.
Figure 7B:
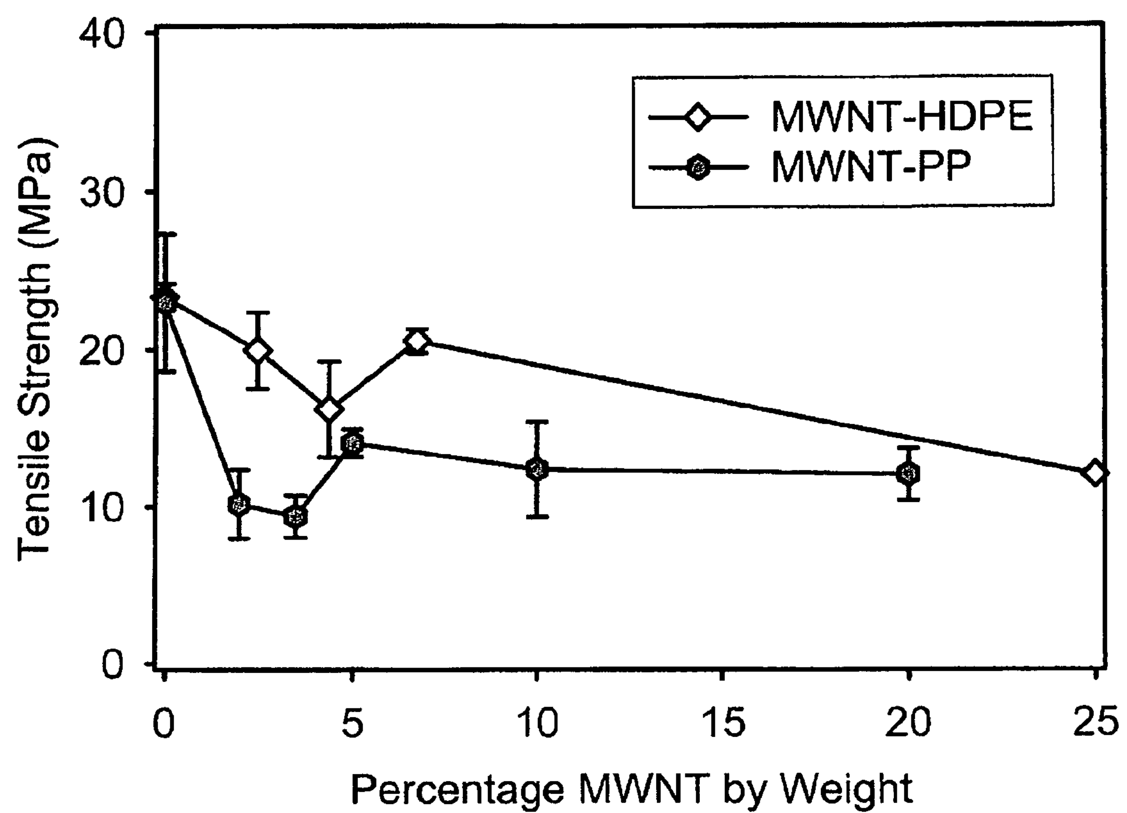
Figure 7C:
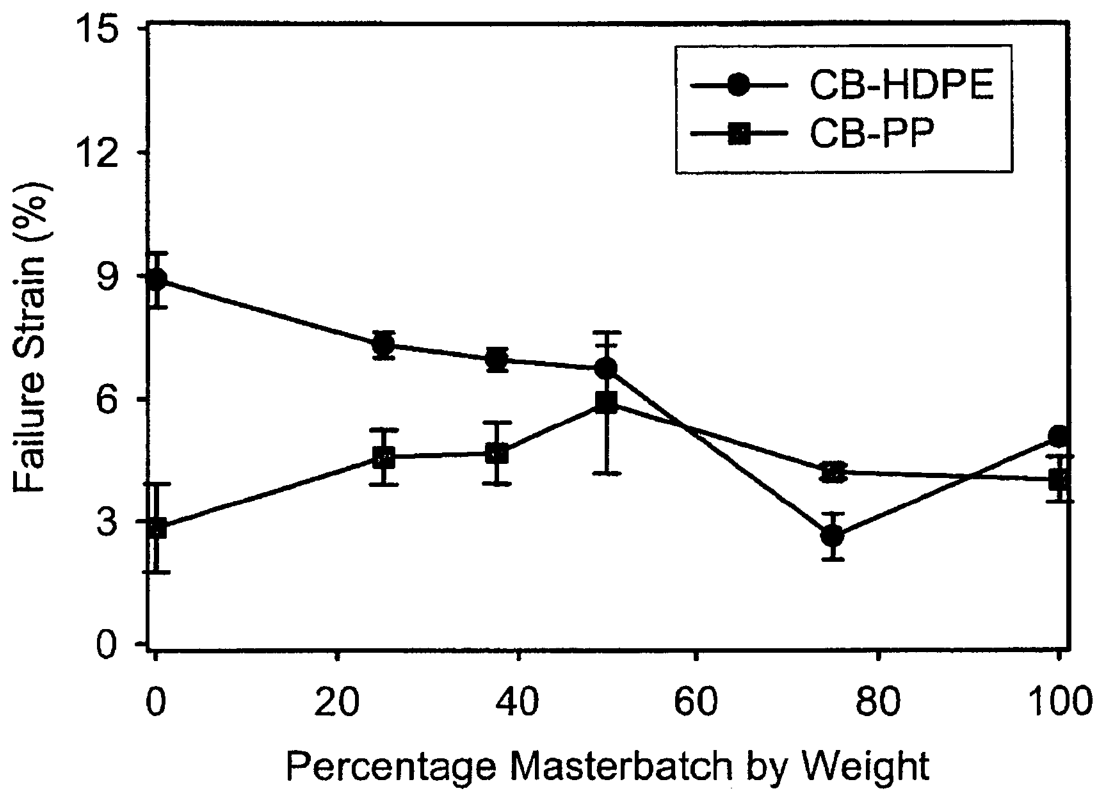
Figure 7D:
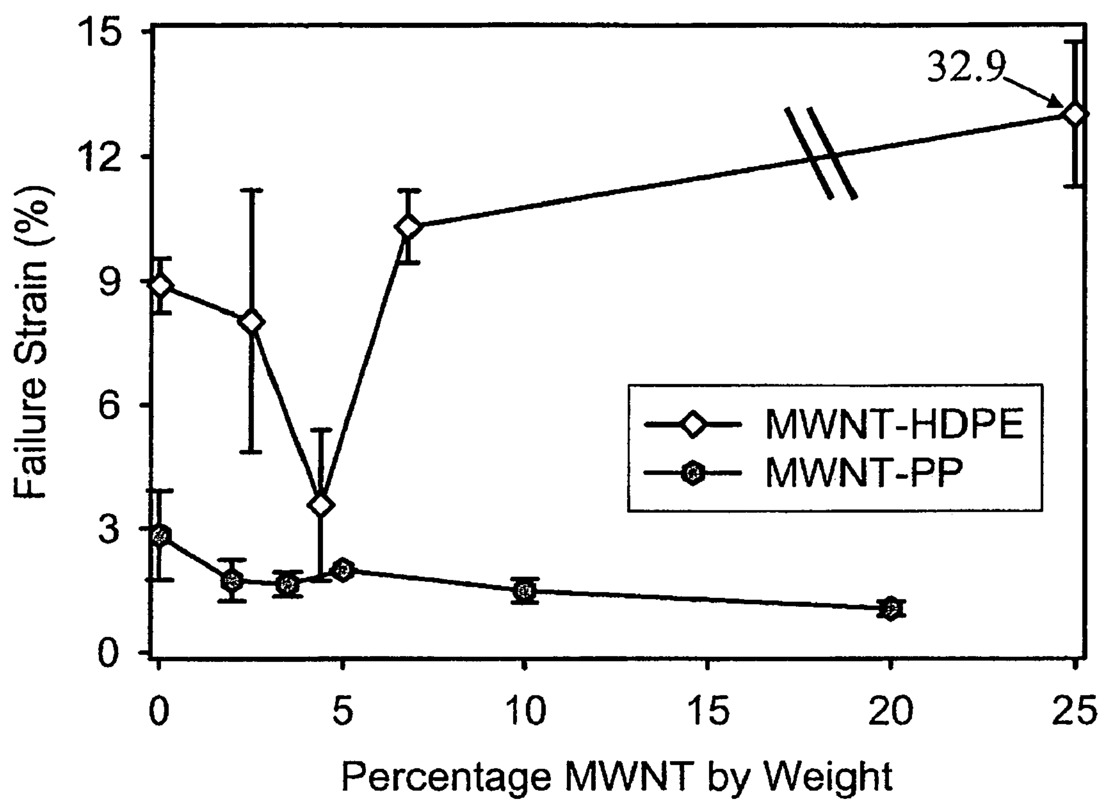
Figure 8A:
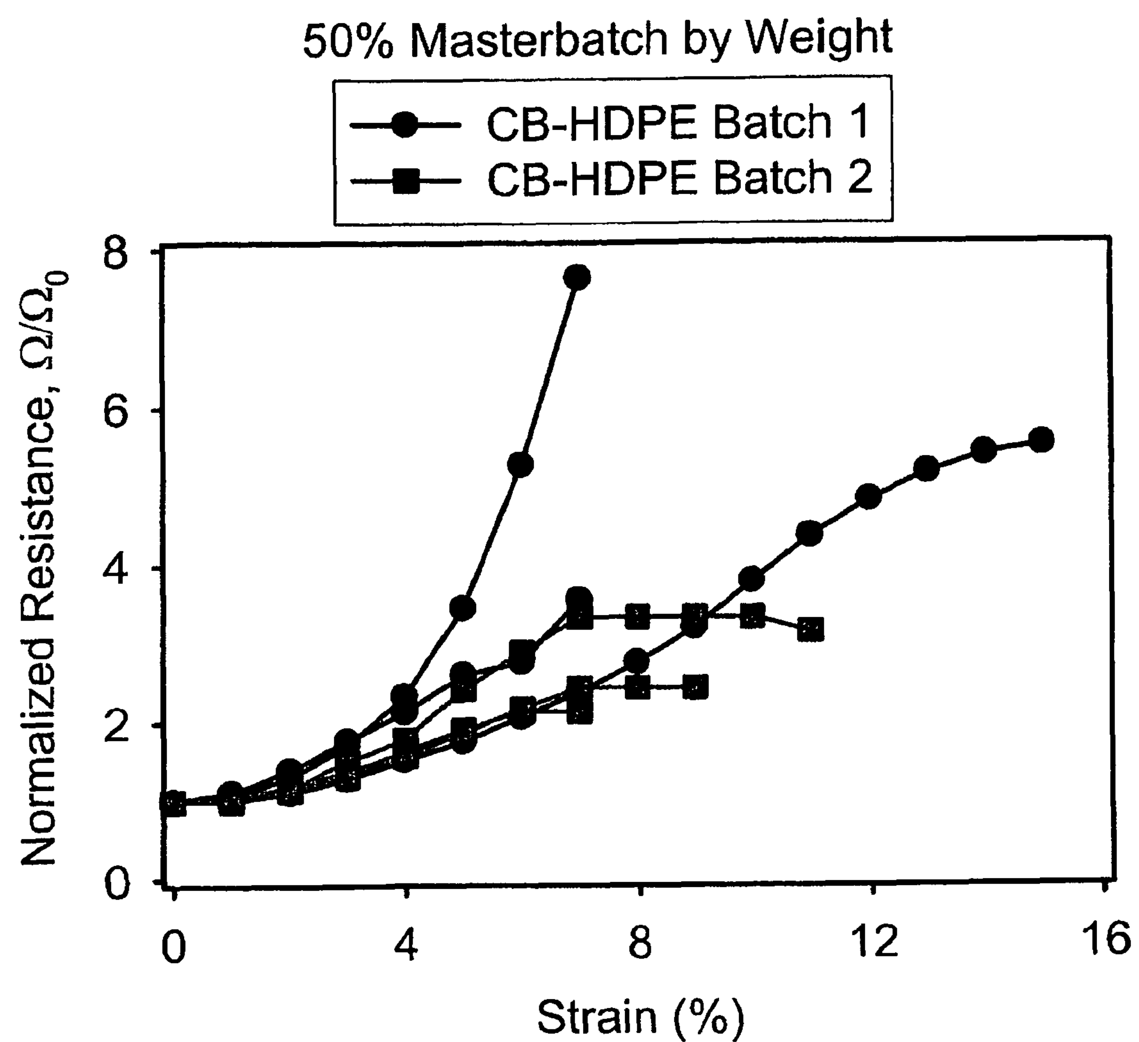
FIG. 8(*a*) is a graph view showing strain-resistivity of a sensor-enabled geosynthetic material constructed in accordance with the present invention.
Figure 8B:
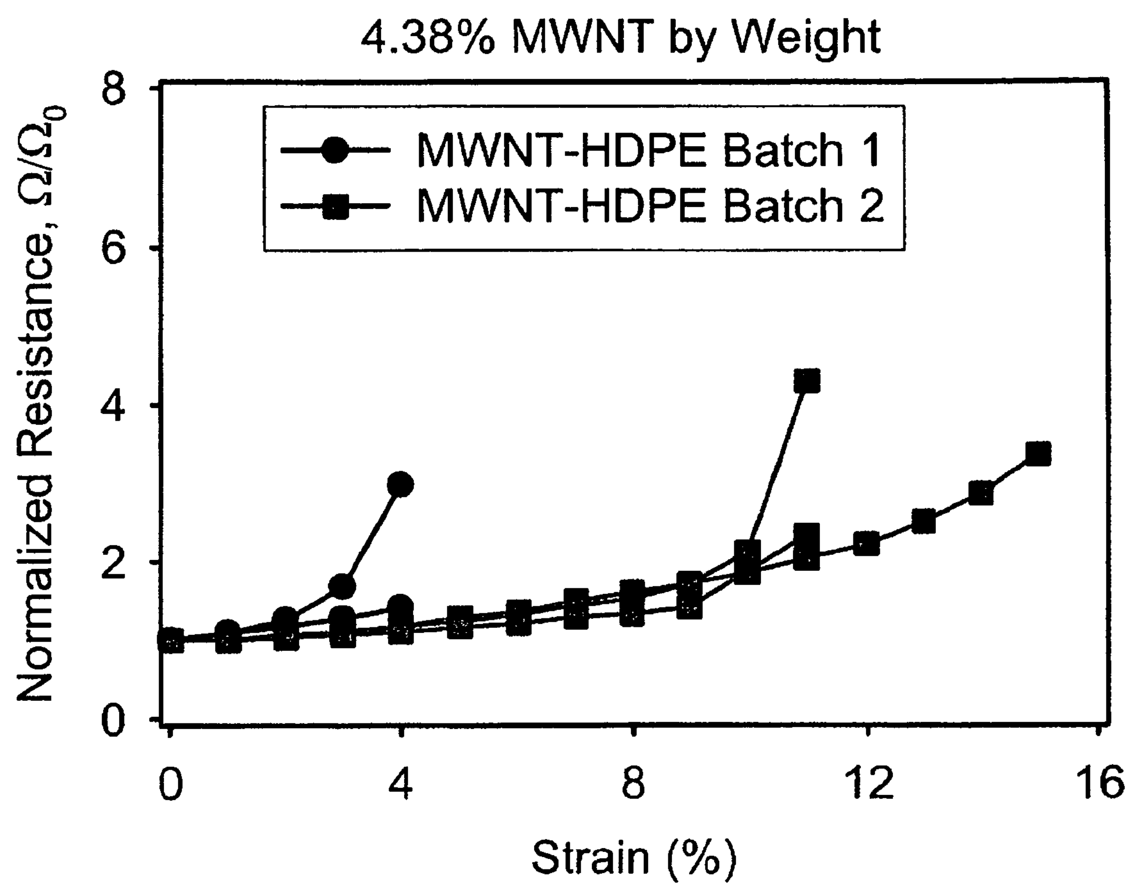
Figure 8C:
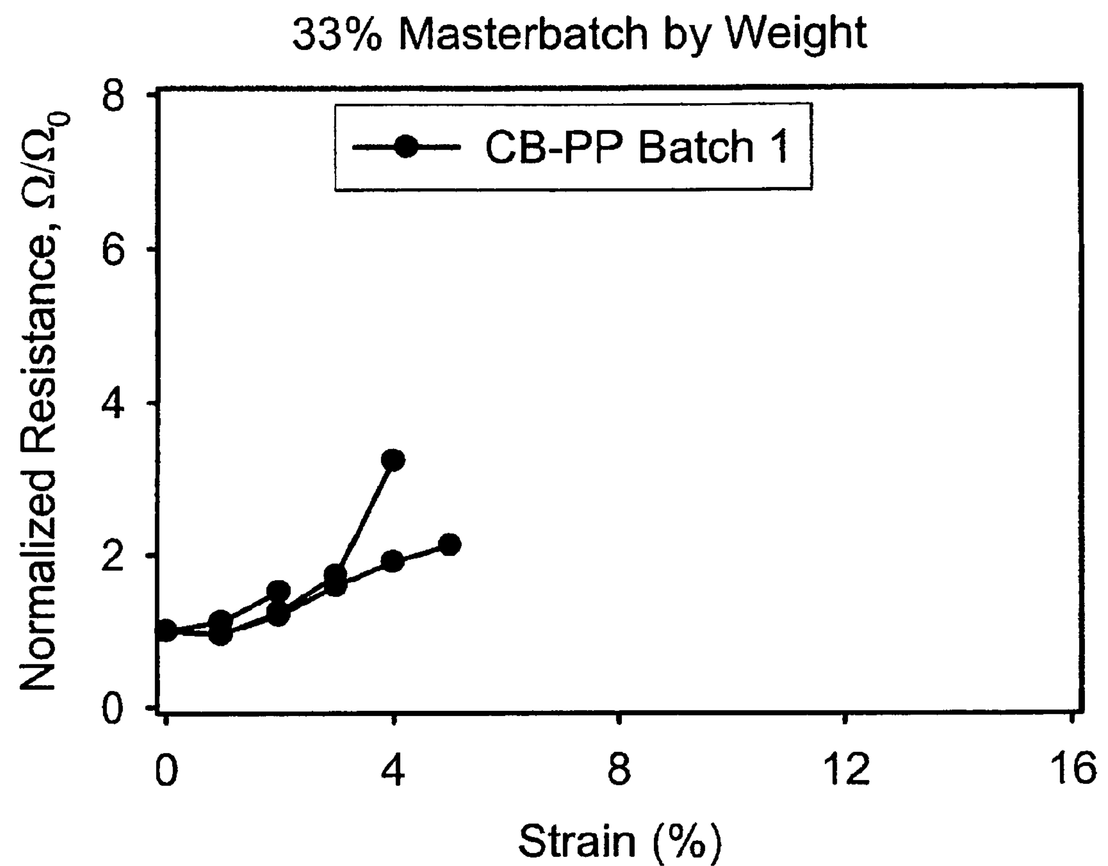
Figure 8D:
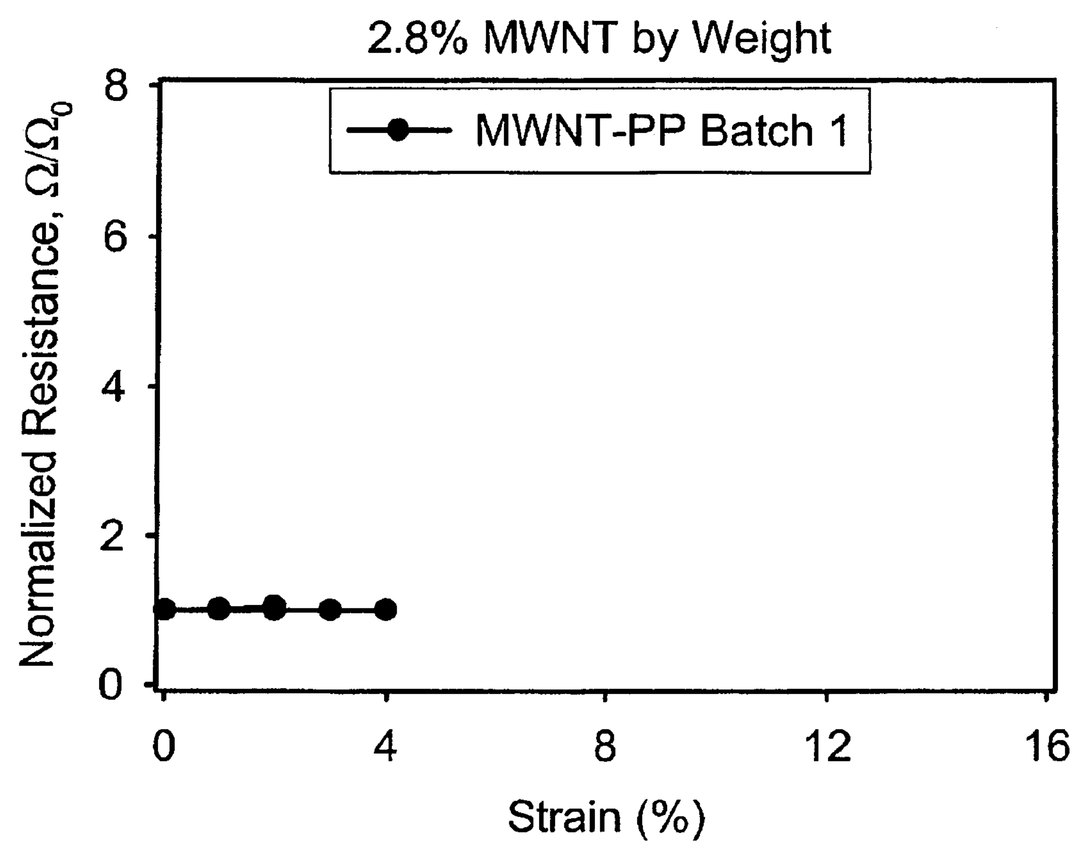

FIGS. 7*c* and 7*d* show failure strains obtained for the CB-filled and NT-filled specimens. Results shown in FIGS. 7*c* and 7*d* indicate that the presence of conductive fillers (i.e. both CB and NT fillers) could reduce the failure strain of the HDPE polymer significantly. For instance, results shown in FIG. 7*c* indicate that CB-filled HDPE specimens with masterbatch-to-virgin ratio greater than 50% are substantially more brittle than the original material. This ratio for the NT-filled PP specimens is about 5% masterbatch or 1.25% filler concentration (FIG. 7*d*).

Comparison of results shown in FIGS. 7*c* and 7*d* indicates that the addition of conductive fillers to virgin PP polymers did not have the same magnitude of deleterious effects with respect to failure strain as those observed for HDPE polymers. In fact, results shown in FIG. 7*c* indicate that failure strain of CB-filled PP specimens increased with the amount of CB filler to an optimum value corresponding to 50% masterbatch-to-virgin polymer weight ratio. On the other hand, failure strain values of NT-filled PP specimens gradually decreased from about 3% for virgin polymers to slightly more than 1% for specimens with 20% NT filler by weight. The reasons for the qualitatively different responses could be related to one or more of the following factors: the differences in the compatibility of masterbatch PP resin with the virgin polymer resin, quality of dispersion in different conductive-filled materials (FIG. 4), or finally, quality of interfacial adhesion in the CB-filled materials as compared to the NT-filled specimens. Complex trends in the mechanical properties of filled polymers as a result of dispersing carbon black have also been reported in previous studies.

Test Series III: Strain-Conductivity Response of SEG Specimens

FIG. 8 shows strain-resistivity results obtained for the SEG specimens with optimal conductive filler concentration values as determined from Test Series I. The CB masterbatch-to-virgin polymer ratio and NT filler concentration values for these specimens are indicated on the plots. Results shown in FIGS. 8*a* and 8*b* indicate that the resistivity (or conductivity) responses of both NT-filled and CB-filled HDPE specimens are strain sensitive. The CB-filled HDPE specimens show both greater strain sensitivity and slightly greater scatter in data than the NT-filled specimens. One possible explanation for the reduced strain sensitivity of NT-filled specimens compared to that of CB-filled specimens is that the NT particles have significantly larger aspect ratios than the CB aggregates (see FIG. 4). This enables the long, rod-shape NT particles to maintain their contact with each other once the composite specimen is subjected to tensile strain. As a result, the resistivity of NT-filled polymer specimens undergoes little change until the strain in the specimen reaches significantly greater values compared to those of the CB-filled specimens. Results shown in FIG. 8*c* indicate that the resistivity (or conductivity) responses of the CB-filled PP specimens are also strain sensitive. However, the strain-sensitivity of the conductivity of NT-filled PP specimens was found to be negligible (FIG. 8*d*). These results indicate that the NT aggregates developed a well-connected 3D conductive network in the PP host that maintained a significant portion of its conductive pathways over the strain magnitudes applied to the specimens. As a result, the resistivity of the specimens was not sensibly affected when they were subjected to tensile loading.

An interesting aspect of the results shown in FIG. 8 is that a sizeable magnitude of strain sensitivity was obtained in polyolefins (i.e. PP and HDPE), which are used in geogrids, and at relatively low strain values that are of interest in geosynthetic engineering. For instance, except for the NT/PP specimens (FIG. 8*d*), the results shown in FIG. 8 indicate that an increase in electrical resistance as great as ~100% (or greater) could be achieved for both HDPE and PP specimens at strain $\epsilon$=4%. These results indicate that the SEG technology (with further refinements in the manufacturing technique to reduce scatter in data) holds promise as a novel approach to measuring geosynthetic strain in a variety of field applications. At the same time, the same results indicate that the sample-to-sample reproducibility needs to be improved in order to improve the accuracy and reliability of this technology.

Test Series IV: Tensile Response (ASTM D6637) of SEG Specimens

Figure 9A:
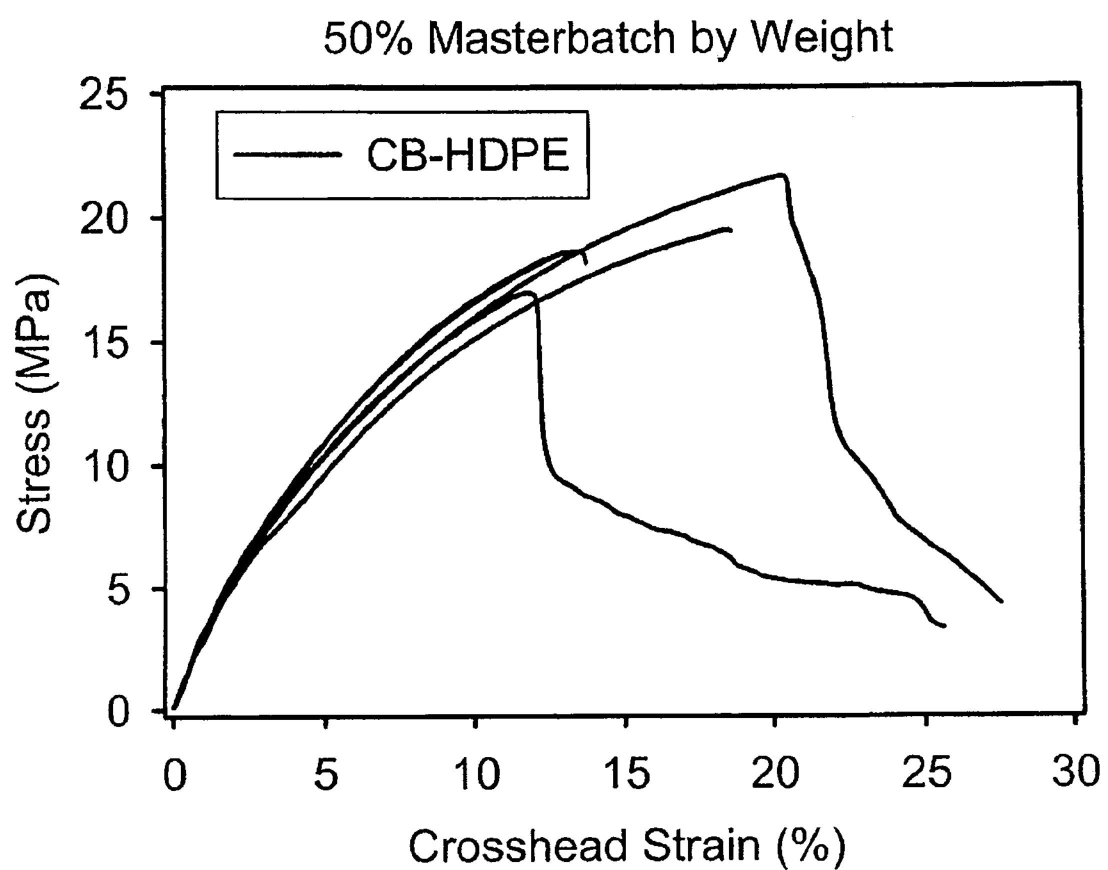
FIG. 9(*a*) is a graph view showing tensile responses of a sensor-enabled geosynthetic material constructed in accordance with the present invention.
Figure 9B:
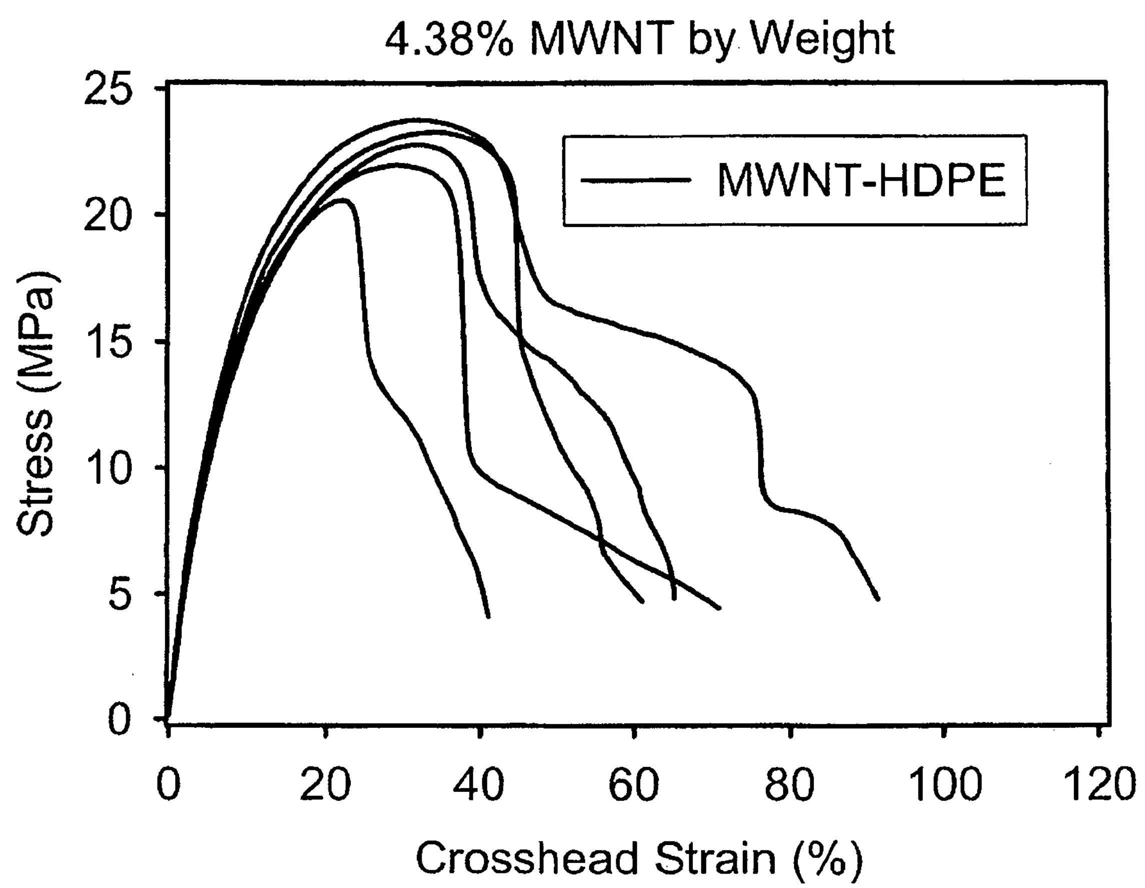

Tensile test results on HDPE SEG specimens according to the ASTM D6637 test protocol are shown in FIG. 9, which indicate a fairly consistent mechanical response for both CB-filled and NT-filled specimens prior to their peak strength. Most of the specimens exhibited a ductile and strain-softening behavior beyond their peak strength. Results shown in FIG. 9 indicate that SEG specimens developed in this study maintain mechanical properties (i.e. ductility and tensile strength) that are suitable for reinforcement applications.

From the above description, it is clear that the present invention is well adapted to carry out the objectives and to attain the advantages mentioned herein as well as those inherent in the invention. While presently preferred embodiments of the invention have been described for purposes of this disclosure, it will be understood that numerous changes may be made which will readily suggest themselves to those skilled in the art and which are accomplished within the spirit of the invention disclosed and claimed.

What is claimed is:

1. A method of measuring geometric strains of a geosynthetic structure, comprising the steps of:

providing a geosynthetic structure fabricated from a sensor-enabled geosynthetic material, the geosynthetic structure selected from the group consisting of a geogrid and a geomembrane;

selecting a measuring location of the geosynthetic structure to measure the geometric strain; and determining the geometric strains of the geosynthetic structure at the measuring location.

2. The method of claim 1 further comprising the step of:

attaching conductive leads to the geosynthetic structure to provide conductivity data; and manipulating the conductivity data to provide the geometric strains applied to the geosynthetic structure.

3. The method of claim 1 wherein the sensor-enabled geosynthetic material comprises:

a polymeric material; and an electrically conductive filler combined with the polymeric material to provide the sensor-enabled geosynthetic material, the sensor-enabled geosynthetic material having a predetermined concentration of the electrically conductive filler so as to provide the sensor-enabled geosynthetic material with an electrical conductivity and a strain sensitivity within a percolation region.

4. The method claim 3 wherein the polymeric material is a polyolefin.

5. The method claim 4 wherein the polyolefin is selected from the group consisting of polypropylene, polyethylene, and combinations thereof.

6. The method claim 3 wherein the electrically conductive filler is selected from the group consisting of metal powders, conductive carbon black, carbon fiber, carbon nanotubes, and combinations thereof.

7. The method of claim 3 wherein the predetermined concentration of the electrically conductive filler in the sensor-enabled geosynthetic material is the highest concentration that allows the sensor-enabled geosynthetic material to remain in the percolation region.

8. The method of claim 3 wherein the predetermined concentration of the electrically conductive filler in the sensor-enabled geosynthetic material is in a range of from about 0.01 wt % to about 30 wt %.

9. The method of claim 3 wherein the predetermined concentration of the electrically conductive filler in the sensor-enabled geosynthetic material is within a range of about 5 wt % of the percolation region.

10. The method of claim 1 wherein a plurality of measuring locations of the geosynthetic product are selected to measure their geometric strains.

11. The method of claim 10 wherein the geometric strains of the plurality of measuring locations are measured simultaneously.

12. A geosynthetic structure constructed from a sensor-enabled geosynthetic material, comprising:

a geosynthetic structure constructed from a polymeric material, the geosynthetic structure selected from the group consisting of a geogrid and a geomembrane; and an electrically conductive filler combined with the polymeric material to provide a sensor-enabled geosynthetic material wherein the entire geosynthetic structure is constructed from the sensor-enabled geosynthetic material, the sensor-enabled geosynthetic material having a predetermined concentration of the electrically conductive filler so as to provide the sensor-enabled geosynthetic material with an electrical conductivity and a strain sensitivity within its percolation region.

13. The sensor-enabled geosynthetic material of claim 12 wherein the polymeric material is a polyolefin.

14. The sensor-enabled geosynthetic material of claim 13 where in the polyolefin is selected from the group consisting of polypropylene, polyethylene, and combinations thereof.

15. The sensor-enabled geosynthetic material of claim 12 wherein the electrically conductive filler is selected from the group consisting of metal powders, conductive carbon black, graphite fiber, carbon nanotubes, and combinations thereof.

16. The sensor-enabled geosynthetic material of claim 12 wherein the predetermined concentration of the electrically conductive filler in the sensor-enabled geosynthetic material is the highest concentration that allows the sensor-enabled geosynthetic material to remain in the percolation region.

17. The sensor-enabled geosynthetic material of claim 12 wherein the predetermined concentration of the electrically conductive filler in the sensor-enabled geosynthetic material is in a range of from about 0.01 wt % to about 30 wt %.

18. The sensor-enabled geosynthetic material of claim 12 wherein the predetermined concentration of the electrically conductive filler in the sensor-enabled geosynthetic material is within a range of about 5 wt % of the percolation region.

* * * * *